(12) United States Patent
Zhang et al.

(10) Patent No.: US 12,285,472 B2
(45) Date of Patent: Apr. 29, 2025

(54) SELF-ANTIGEN DISPLAYING NANOPARTICLES TARGETING AUTO-REACTIVE IMMUNE FACTORS AND USES THEREOF

(71) Applicant: THE REGENTS OF THE UNIVERSITY OF CALIFORNIA, Oakland, CA (US)

(72) Inventors: Liangfang Zhang, San Diego, CA (US); Che-Ming Jack Hu, San Diego, CA (US); Jonathan Copp, Cleveland, OH (US); Ronnie H. Fang, Irvine, CA (US); Brian T. Luk, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/505,148

(22) PCT Filed: Aug. 20, 2015

(86) PCT No.: PCT/US2015/046016
§ 371 (c)(1),
(2) Date: Feb. 20, 2017

(87) PCT Pub. No.: WO2016/028965
PCT Pub. Date: Feb. 25, 2016

(65) Prior Publication Data
US 2017/0274059 A1   Sep. 28, 2017

Related U.S. Application Data

(60) Provisional application No. 62/039,601, filed on Aug. 20, 2014.

(51) Int. Cl.
| | | |
|---|---|---|
| *A61K 39/00* | (2006.01) |
| *A61K 9/00* | (2006.01) |
| *A61K 9/51* | (2006.01) |
| *A61K 35/12* | (2015.01) |
| *A61K 39/385* | (2006.01) |
| *A61K 45/06* | (2006.01) |
| *A61K 47/34* | (2017.01) |

(52) U.S. Cl.
CPC ........ *A61K 39/0008* (2013.01); *A61K 9/0014* (2013.01); *A61K 9/0019* (2013.01); *A61K 9/5146* (2013.01); *A61K 9/5184* (2013.01); *A61K 35/12* (2013.01); *A61K 39/385* (2013.01); *A61K 45/06* (2013.01); *A61K 47/34* (2013.01); *A61K 2039/55555* (2013.01); *A61K 2039/6006* (2013.01)

(58) Field of Classification Search
CPC .............. A61K 39/0008; A61K 39/385; A61K 2039/6006; A61K 35/12; A61K 9/5176
See application file for complete search history.

(56) References Cited

U.S. PATENT DOCUMENTS

| | | | |
|---|---|---|---|
| 8,835,387 B2 * | 9/2014 | Chiang .................. A61P 37/00 | |
| | | | 514/12.1 |
| 9,539,210 B2 * | 1/2017 | von Andrian ......... A61K 39/00 |
| 2013/0028962 A1 | 1/2013 | Zhang et al. |
| 2013/0337066 A1 | 12/2013 | Zhang et al. |
| 2017/0095510 A1 | 4/2017 | Lee |

OTHER PUBLICATIONS

Hu, C.E., et al. Nature Nanotech. 2013:8:336-340. (Year: 2013).*
Dhaliwal, G., et al. Am. Fam. Phys .; 69(11):2599-2906 (Year: 2004).*
Garratty, G. Hematol.;1:73-79 (Year: 2009).*
DeNicola, "Anemia-Is it regenerative or non-regenerative?", In: 'Small Animal Hematology', The North American Veterinary Conference, 2006, pp. 485-489 (Year: 2006).*
Packman (Blood Reviews, 2008, vol. 22, pp. 17-31) (Year: 2008).*
Leddy et al, Journal of Clinical Investigation, 1993, vol. 91, pp. 1672-1680 (Year: 1993).*
Hu et al., "Erythrocyte Membrane-Camouflaged Polymeric Nanoparticles as a Biomimetic Delivery Platform," PNAS, 2011, 108(27):10980-10985.
Hu et al., "'Marker-of-Self' Functionalization of Nanoscale Particles Through a Top-Down Cellular Membrane Coating Approach," Nanoscale, 2013, 5(7):2664-2668.
Trapani et al., "Infective, Neoplastic, and Homeostatic Sequelae of the Loss of Perforin Function in Humans," Adv. Exp. Med. Biol., 2007, 601:235-242.
The website downloaded Mar. 20, 2019: https ://rarediseases .info. nih .gov/diseases/6589/hemophagocytic-lymphohistiocytosis#ref_ 7853 (Year: 2019).
Dhaliwal et al., "Hemolytic Anemia," American Family Physician, 2004, 69(11):2599-2606.
Janka et al., "Hemophagocytic Lymphohistiocytosis: Pathogenesis and Treatment," Hematology, 2013, 605-611.

* cited by examiner

*Primary Examiner* — Karen A. Canella
(74) *Attorney, Agent, or Firm* — Eversheds-Sutherland (US) LLP

(57) ABSTRACT

The invention provides a composition, and method of use thereof, comprising self-antigen displaying nanoparticles to target auto-reactive immune components for treating and/or preventing the autoimmune diseases associated therewith. The nanoparticles can also be loaded with cytotoxic drugs for targeted cell killing or with immune-tolerizing compounds to normalize the immune regulation.

13 Claims, 8 Drawing Sheets

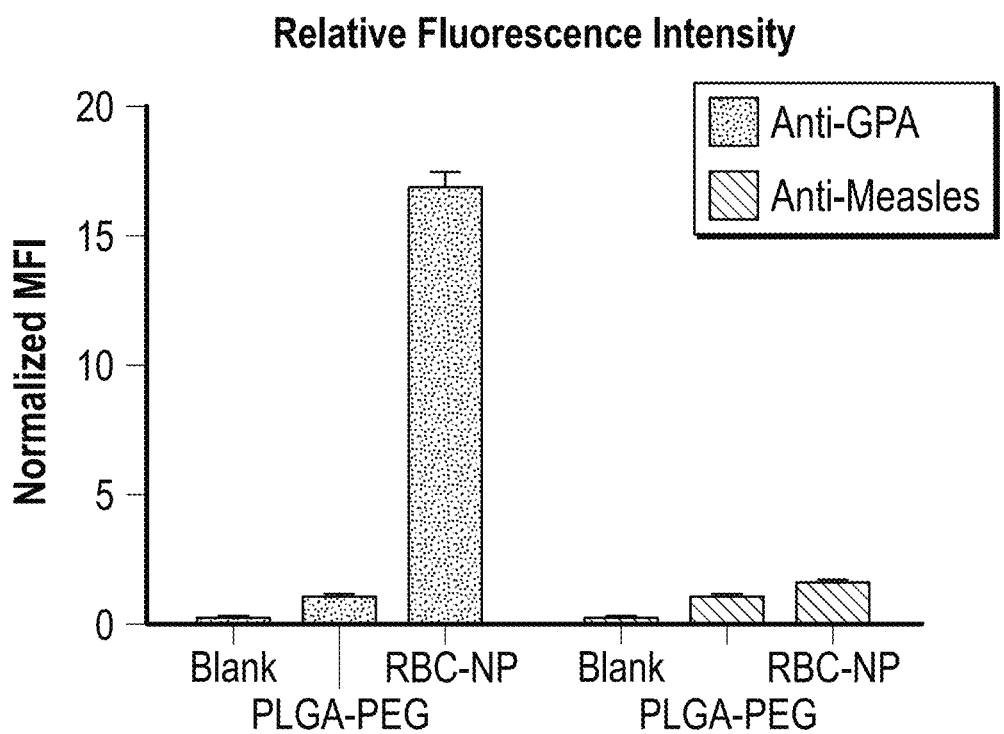
FIG. 2
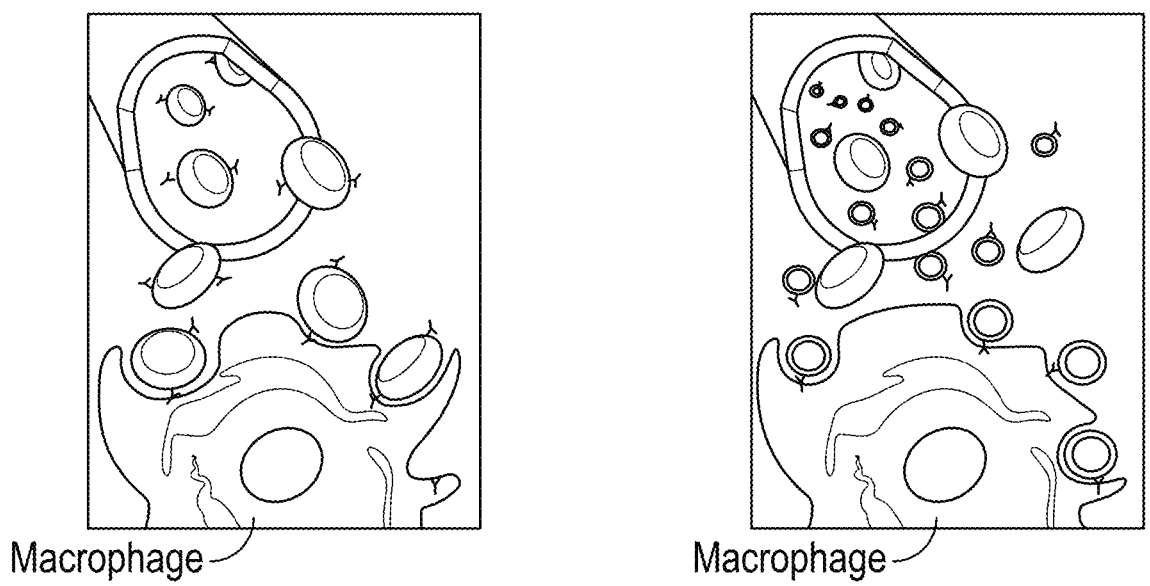
FIG. 3A
FIG. 3B

SELF-ANTIGEN DISPLAYING NANOPARTICLES TARGETING AUTO-REACTIVE IMMUNE FACTORS AND USES THEREOF

CROSS REFERENCE TO RELATED APPLICATION

This application claims the priority benefit of PCT/US2015/046016 filed on Aug. 20, 2015 which claims priority benefit of U.S. provisional application Ser. No. 62/039,601, filed Aug. 20, 2014. The contents of which are hereby incorporated by reference in their entireties.

STATEMENT REGARDING FEDERALLY SPONSORED RESEARCH

This invention was made with government support under R01DK095168 and R25CA1539915 awarded by the National Institutes of Health. The government has certain rights in the invention.

FIELD OF THE INVENTION

The present invention relates to methods and compositions for treating autoimmune disease. More particularly, the invention relates to a method of use of compositions comprising nanoparticles that display self-antigen to target auto-reactive components of autoimmune disease.

BACKGROUND OF THE INVENTION

Autoimmune diseases are diseases in which the body's own immune system is deregulated and mounts an attack against the body's own healthy cells and tissues. Autoimmune diseases can target and damage any organ system of the body and can be a result of overactive T cells, B cells or both in combination. In addition to the cellular activity, almost all autoimmune diseases have established auto-antibodies known to be involved in some way in the disease process. In several of these autoimmune conditions (pemphigus vulgaris, bullous pemphigoid, myasthenia gravis, Guillain-Barre syndrome, anti-phospholipid syndrome, autoimmune hemolytic anemia and immune thrombocytopenic purpura) the specific role that autoantibodies play is known and established. However, despite this knowledge there is no specific treatment available to disrupt auto-self destruction (1,2).

The current treatment standards, such as chemotherapeutic agents, systemic steroids, anti-tumor necrosis factor agents, anti-Interferon agents as well as cytotoxic monoclonal antibodies, function via broad-spectrum immune suppression and fall short of offering specific therapy against the auto-reactive immune factors. All of the existing therapies serve to suppress entire arms of the immune system (knock out B cells, suppress entire adaptive immunity, etc.) without specificity to the aberrant immune components. In addition, response rates for current regimens average 30-50% amongst patients receiving therapy and for many non-responders, the cause for non-response is unknown due to significant genetic heterogeneity (3). As a result, the field of rheumatology is in great need of new, novel therapeutics that target areas of disease with ideally far less significant off-target effects or side effects which include reactivation of latent tuberculosis, progressive multifocal leukoencephalopathy (PML) and severe immunosuppression among others.

Therefore, what are needed are improved methods and compositions for treating autoimmune diseases. The present invention addresses these and other related needs in the art.

SUMMARY OF THE INVENTION

The invention provides compositions, and methods of use thereof, comprising nanoparticles displaying self-antigens to target auto-reactive components of autoimmune disease (immunoglobulins, B cells and T cells). Detailed descriptions of certain embodiments of the composition and nanoparticles are provided in WO2013/052167 and US Publication No. 20130337066, the entire contents of which are incorporated by reference herewith.

In certain embodiments, the invention provides red blood cell (RBC) membrane-cloaked nanoparticles functionalized with RBC antigens, to absorb anti-RBC antibodies and prevent their binding to RBCs. In certain embodiments, a direct antibody test (DAT) (aka Coomb's test) was performed to detect RBC auto-antibodies (the primary autoreactive immune factor in autoimmune hemolytic anemia (AIHA)). Nanoparticles coated in mouse RBC were co-incubated with anti-mouse RBC antibodies for 1 hour and then a standard Coomb's test was carried out. Results demonstrate the ability to neutralize the RBC antibody by preventing macroscopic and microscopic agglutination. In other embodiments, the binding capacity of the membrane coated nanoparticles for absorbed antibody was performed. Results demonstrate a saturation capacity of approximately 60 µg of antibody per 250 µg of nanoparticles. Specificity between the anti-RBC antibodies and RBC antigens displaying nanoparticles was also demonstrated.

The invention further provides that the nanoparticles can also be loaded with cytotoxic drugs for targeted cell killing or with immune-tolerizing compounds to normalize the immune regulation. In certain embodiments, the invention provides that administration of the RBC antigen displaying nanoparticles reduces anemia symptoms upon anti-RBC antibody injection in in vivo studies.

In certain embodiments, the present invention further provides that the inventive nanoparticle comprises a releasable cargo that can be located in any place inside or on the surface of the nanoparticle. A trigger for releasing the releasable cargo from the inventive nanoparticle includes, but is not limited to, contact between the nanoparticle and a target cell, tissue, organ or subject, or a change of an environmental parameter, such as the pH, ionic condition, temperature, pressure, and other physical or chemical changes, surrounding the nanoparticle. In certain embodiments, the releasable cargo comprises one or more therapeutic agent, prophylactic agent, diagnostic or marker agent, prognostic agent, e.g., an imaging marker, or a combination thereof. In yet certain other embodiments, the releasable cargo is a metallic particle, a polymeric particle, a dendrimer particle, or an inorganic particle.

In certain embodiments, the nanoparticle of the present invention comprises the cellular plasma membrane derived from a red blood cell and an inner core comprising poly (lactic-co-glycolic acid) (PLGA), wherein the nanoparticle substantially lacks hemoglobin. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the hemoglobin of the red blood cell from which the plasma membrane is derived.

Such inventive nanoparticle has a half-life in blood circulation in vivo at least about 2-5 times the half-life of a polyethylene glycol (PEG)-coated, comparable nanoparticle. In certain embodiments, such inventive nanoparticle has a half-life in blood circulation in vivo for at least about 5 to about 40 hours or longer.

In certain embodiments, the inventive nanoparticle substantially lacks immunogenicity to a species or subject from which the cellular membrane is derived. For example, the present nanoparticle can lack, in terms of types and/or quantities, at least 10%, 20%, 30%, 40%, 50%, 60%, 70%, 80%, 90%, 95%, 96%, 97%, 98%, 99% or 100% of the immunogenicity to a species or subject from which the cellular membrane is derived.

The present invention further provides a medicament delivery system, and a pharmaceutical composition comprising the inventive nanoparticle. In certain embodiments, the medicament delivery system and the pharmaceutical composition of the present invention further comprise one or more additional active ingredient and a medically or pharmaceutically acceptable carrier or excipient that can be administered along with or in combination with the nanoparticle of the present invention.

The present invention further provides a method for treating and/or preventing an autoimmune disease or condition in a subject in need using the inventive nanoparticles, the medicament delivery system, or the pharmaceutical composition comprising the same. In certain embodiments, the cellular membrane of the nanoparticle used for the inventive method is derived from a cell of the same species of the subject or is derived from a cell of the subject. In certain embodiments, the cellular membrane of the nanoparticle used for the inventive method is derived from a red blood cell of the same species of the subject and the red blood cell has the same blood type of the subject. In other embodiments, the cellular membrane of the nanoparticles used for the inventive methods is derived from a variety of biological membranes and/or cellular component as described below. In certain embodiments, the nanoparticle, the medicament delivery system, or the pharmaceutical composition is administered via any suitable administration route. For example, the nanoparticle, the medicament delivery system, or the pharmaceutical composition can be administered via an oral, nasal, inhalational, parental, intravenous, intraperitoneal, subcutaneous, intramuscular, intradermal, topical, or rectal route.

In other embodiments, the nanoparticle is administered via a medicament delivery system. In yet other embodiments, the inventive method further comprises administering another active ingredient, or a pharmaceutically acceptable carrier or excipient, to the subject in need. The inventive method further provides that the nanoparticle of the present invention can be administered systemically or to a target site of the subject in need. Use of an effective amount of nanoparticles of the present invention for the manufacture of a medicament for treating or preventing an autoimmune disease or condition in a subject in need is also provided.

In one aspect, the present invention provides for a method for treating or preventing an autoimmune disease or condition in a subject, which method comprises administering, to a subject in need, or to cells of said subject, an effective amount of a nanoparticle comprising a) an inner core comprising a non-cellular material, b) an outer surface comprising a cellular membrane comprising a self-antigen that targets an auto-reactive component of said autoimmune disease or condition, wherein when said cellular membrane is derived from a red blood cell, said method is not used for treating or preventing an autoimmune hemolytic disease or condition in said subject.

In another aspect, the present invention is directed to a use of an effective amount of a nanoparticle for the manufacture of a medicament for treating or preventing an autoimmune disease or condition in a subject, wherein said nanoparticle comprises a) an inner core comprising a non-cellular material, b) an outer surface comprising a cellular membrane comprising a self-antigen that targets an auto-reactive component of said autoimmune disease or condition, and when said cellular membrane is derived from a red blood cell, said medicament is not used for treating or preventing an autoimmune hemolytic disease or condition in said subject.

In still another aspect, the present invention provides for a combination for treating or preventing an autoimmune disease or condition in a subject, which combination comprises an effective amount of a nanoparticle and an effective amount of a second prophylactic or therapeutic agent for treating or preventing an autoimmune disease or condition in a subject, wherein said nanoparticle comprises a) an inner core comprising a non-cellular material, b) an outer surface comprising a cellular membrane comprising a self-antigen that targets an auto-reactive component of said autoimmune disease or condition, and when said cellular membrane is derived from a red blood cell, said combination is not used for treating or preventing an autoimmune hemolytic disease or condition in said subject. The present invention also provides for a pharmaceutical composition comprising the combination and a method for treating or preventing an autoimmune disease or condition in a subject using the combination or the pharmaceutical composition comprising the combination.

In some embodiments, the present nanoparticles, medicament delivery systems, pharmaceutical compositions and methods, can be used to deliver the exemplary medications listed in the Orange Book: Approved Drug Products with Therapeutic Equivalence Evaluations (Current through March 2012) published by the U.S. Food and Drug Administration, the exemplary medications listed in The Merck Index (a U.S. publication, the printed 14th Edition, Whitehouse Station, N.J., USA) and its online version (The Merck Index Online$^{SM}$, Last Loaded on Web: Tuesday, May 1, 2012), and the exemplary medications listed in Biologics Products & Establishments published by the U.S. Food and Drug Administration, and can be used to treat or prevent the corresponding diseases and disorders.

In some aspects, the present disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

Those of skill in the art will understand that the drawings, described below, are for illustrative purposes only. The drawings are not intended to limit the scope of the present teachings in any way.

FIG. 2. Fluorescently labeled RBC membrane cloaked nanoparticles exhibit superior affinity to anti-glycophorin. Anti-glycophorin A hybridoma cells as compared to anti-measles hybridoma cells. The superior affinity can be attributed to the b-cell receptor specific to glycophorin A, which is an antigen on red blood cell membranes.

FIGS. 3A-3B. Schematic representation of RBC antibody nanosponges (RBC-ANS) neutralizing anti-RBC antibodies (anti-RBC). FIG. 3(A) Anti-RBC opsonize RBCs for extravascular hemolysis, via phagocytosis, as observed in autoimmune hemolytic anemia and drug-induced anemia. FIG. 3(B) RBC-ANS absorb and neutralize anti-RBC, thereby protecting RBCs from phagocytosis.

FIG. 4(A). TEM image demonstrated the core-shell structure of RBC-ANS (scale bar=150 nm). FIG. 4(B). Size and surface zeta-potential of pure PLGA cores, RBC-ANS, and RBC-ANS bound with anti-RBC. FIG. 4(C). 250 μg of RBC-ANS incubated with 5 serial dilutions of fluorescent anti-RBC demonstrated particle saturation at ~27 μg of antibody, corresponding to ~9:1 particle/antibody mass ratio. FIG. 4(D). Equivalent amounts of RBC-ANS incubated with anti-RBC or anti-Fc demonstrated significantly greater specific binding as compared to nonspecific binding. The corresponding PEGylated PLGA nanoparticle (PEG-NP) incubated with anti-RBC served as a negative control. FIG. 4(E). Comparison of anti-RBC binding kinetics to a fixed amount of RBC-ANS or RBC ghosts. Inset represents relative binding capacity of RBC-ANS versus RBC ghosts at saturation. FIG. 4(F). Relative binding capacity of RBC-ANS in PBS versus in serum at saturation.

FIG. 5(A). Flow-cytometry histograms of RBC-ANS (from left to right: 1000, 500, 250, 100, 50 and 0 μg) pre-incubated with 50 μg FITC-anti-RBC prior to mixing with 5% RBC solution demonstrated dose-dependent neutralization of anti-RBC. FIG. 5(B). Mean fluorescence intensity of samples in FIG. 5(A). FIG. 5(C). Flow-cytometry histograms of RBC-ANS (from left to right: 1000, 500, 250, 100, 50 and 0 μg) co-incubated with 50 μg FITC-anti-RBC and 5% RBC solution demonstrated dose-dependent, competitive neutralization of anti-RBC. FIG. 5(D). Mean fluorescence intensity of samples in FIG. 5(C). FIGS. 5(E-I). Varying amounts of RBC-ANS (from E to I: 0, 25, 50, 100, and 250 μg) were co-incubated with 15.6 μg anti-RBC (primary antibody) and 5% RBC solution, followed by adding equivalent dose of anti-Fc (agglutinating secondary antibody). The samples were then imaged by light microscope at 10× magnification, demonstrating dose related inhibition of RBC agglutination by RBC-ANS.

DETAILED DESCRIPTION OF THE INVENTION

Figure 1:
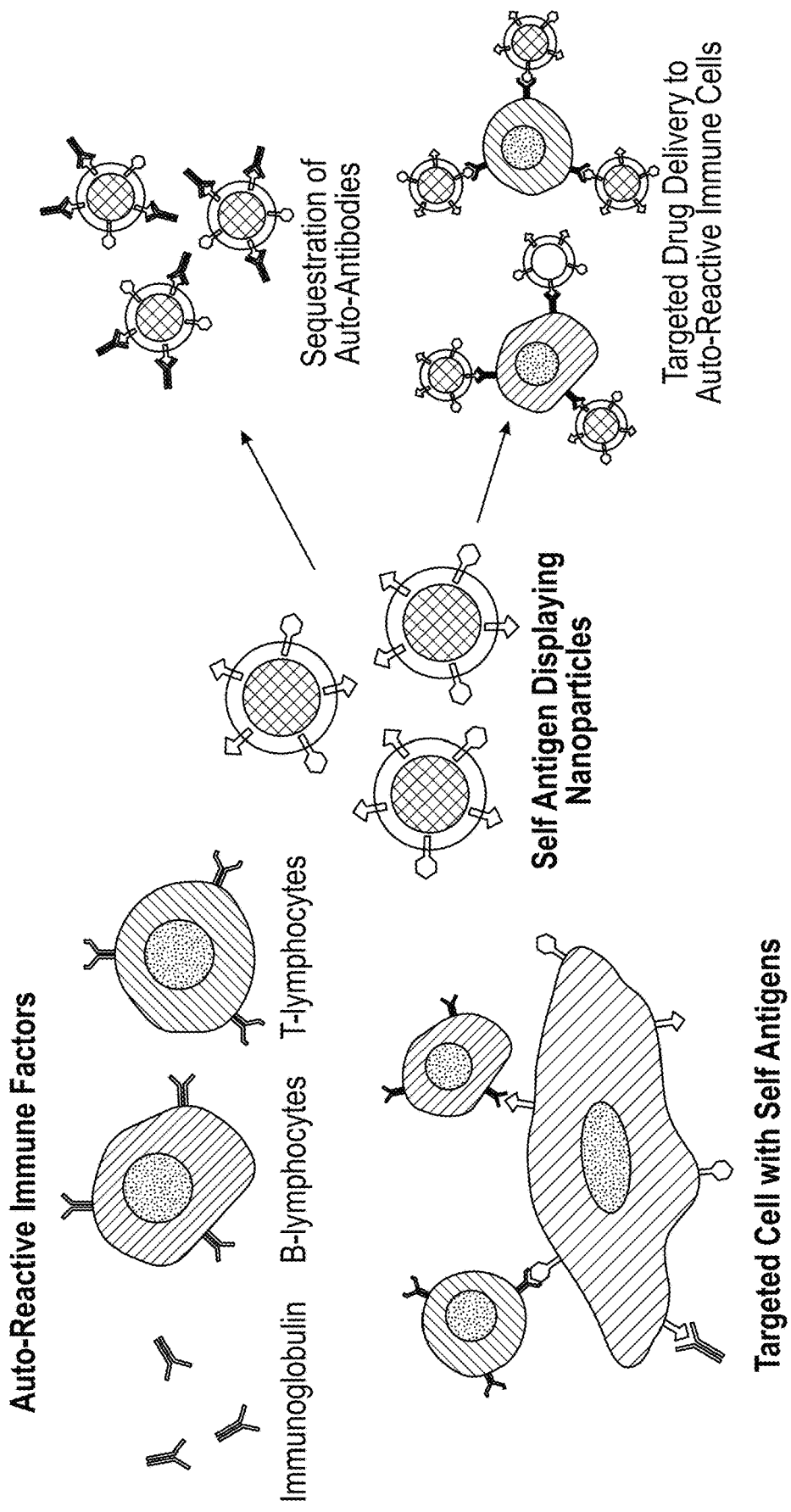
FIG. 1. Schematics of self-antigen displaying nanoparticles and its application in treating auto-reactive immune factors.

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, Molecular Cloning: A Laboratory Manual, 2nd ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); and Remington, The Science and Practice of Pharmacy, $20^{th}$ ed., (Lippincott, Williams & Wilkins 2003).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "cellular membrane" as used herein refers to a biological membrane enclosing or separating structure acting as a selective barrier, within or around a cell or an emergent viral particle. The cellular membrane is selectively permeable to ions and organic molecules and controls the movement of substances in and out of cells. The cellular membrane comprises a phospholipid uni- or bilayer, and optionally associated proteins and carbohydrates. As used herein, the cellular membrane refers to a membrane obtained from a naturally occurring biological membrane of a cell or cellular organelles, or one derived therefrom. As used herein, the term "naturally occurring" refers to one existing in nature. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the unilamellar or multilamellar cellular membrane of the nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

As used herein, the term "synthetic membrane" or "artificial membrane" refers to a man-made membrane that is produced from organic material, such as polymers and liquids, as well as inorganic materials. A wide variety of synthetic membranes are well known in the art.

As used herein, the term "membrane derived from a virus" refers to viral envelopes that cover the nucleic acid or protein capsids of a virus, and typically contain cellular membrane proteins derived from portions of the host cell membrane (phospholipid and proteins) and include some viral glycoproteins. The viral envelop fuses with the host's membrane, allowing the capsid and viral genome to enter and infect the host.

The term "nanoparticle" as used herein refers to nanostructure, particles, vesicles, or fragments thereof having at least one dimension (e.g., height, length, width, or diameter) of between about 1 nm and about 10 μm. For systemic use, an average diameter of about 50 nm to about 500 nm, or 100 nm to 250 nm may be preferred. The terms "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. The invention contemplates any nanoparticles now known and later developed that can be coated with the membrane described herein.

The terms "pharmaceutically active" as used herein refer to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

The terms "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

The terms "pharmaceutically acceptable salt" as used herein refer to acid addition salts or base addition salts of the compounds, such as the multi-drug conjugates, in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zürich, 2002; Berge et al., J Pharm. Sci. 66:1, 1977). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.,* 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

The terms "pharmaceutically acceptable carrier" as used herein refers to an excipient, diluent, preservative, solubilizer, emulsifier, adjuvant, and/or vehicle with which a compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20$^{th}$ ed., (Lippincott, Williams & Wilkins 2003). Except insofar as any conventional media or agent is incompatible with the active compound, such use in the compositions is contemplated.

The term "phospholipid", as used herein, refers to any of numerous lipids contain a diglyceride, a phosphate group, and a simple organic molecule such as choline. Examples of phospholipids include, but are not limited to, phosphatidic acid (phosphatidate) (PA), phosphatidylethanolamine (cephalin) (PE), phosphatidylcholine (lecithin) (PC), phosphatidylserine (PS), and phosphoinositides which include, but are not limited to, phosphatidylinositol (PI), phosphatidylinositol phosphate (PIP), phosphatidylinositol bisphosphate (PIP2) and phosphatidylinositol triphosphate (PIP3). Additional examples of PC include DDPC, DLPC, DMPC, DPPC, DSPC, DOPC, POPC, DRPC, and DEPC as defined in the art.

As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the sections below. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition such as an infection or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "combination" refers to either a fixed combination in one dosage unit form, or a kit of parts for the combined administration where a compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

Other objects, advantages and features of the present invention will become apparent from the following specification taken in conjunction with the accompanying drawings.

B. Compositions and Methods for Treating or Preventing an Autoimmune Disease or Condition in a Subject In one aspect, the present invention provides for a method for treating or preventing an autoimmune disease or condition in a subject, which method comprises administering, to a subject in need, or to cells of said subject, an effective amount of a nanoparticle comprising a) an inner core comprising a non-cellular material, b) an outer surface comprising a cellular membrane comprising a self-antigen that targets an auto-reactive component of said autoimmune disease or condition, wherein optionally when said cellular membrane is derived from a red blood cell, said method is not used for treating or preventing an autoimmune hemolytic disease or condition in said subject.

The present methods can be used to treat or prevent an autoimmune disease or condition in any suitable subject. In some embodiments, the mammal is a human. In other embodiments, the mammal is a non-human mammal, including a pet, a farm animal, an economic animal, a sport animal and an experimental animal, a cat, a dog, a horse, a cow, an ox, a pig, a donkey, a sheep, a lamb, a goat, a mouse, a rabbit, or a primate, including a monkey and a chimpanzee.

In some embodiments, the present methods can be used for treating an autoimmune disease or condition in any suitable subject. In other embodiments, the present methods can be used for preventing an autoimmune disease or condition in any suitable subject.

The nanoparticle used in the present methods can target any suitable auto-reactive component. For example, the nanoparticle can target an auto-reactive immunoglobulin, or an auto-reactive cell, e.g., an auto-reactive B cell, an auto-reactive T cell, or an auto-reactive lymphocyte.

The cellular membrane of the nanoparticle used in the present methods can be derived from any suitable cell or cellular source. For example, the cellular membrane can be derived from a red blood cell, a platelet, an epidermal cell, an epidermal-dermal junction, myelin of a nerve or a Schwann cell, a pancreatic islet cell, a mitochondrial or a bacterium.

In some embodiments, the cellular membrane is derived from a red blood cell. Such nanoparticle can be used to sequester or neutralize an anti-RBC auto-reactive cell or autoantibody, e.g., an anti-glycophorin A (GPA) autoantibody or an anti-ganalioside autoantibody associated with Guillain-Barr syndrome.

In some embodiments, the cellular membrane is derived from a platelet. Such nanoparticle can target any suitable anti-platelet auto-reactive cell or autoantibody, e.g., an anti-platelet autoantibody responsible for thrombocytopenia, preventing the activation and destruction of functional platelets, hemorrhage or microthrombi in thrombocytopenic purpura.

In some embodiments, the cellular membrane is derived from an epidermal cell. Such nanoparticle can target any suitable anti-epidermal cell auto-reactive cell or autoantibody, e.g., an anti-desmoglein autoantibody responsible for pemphigus vulgaris.

In some embodiments, the cellular membrane is derived from an epidermal-dermal junction. Such nanoparticle can target any suitable anti-epidermal-dermal junction auto-reactive cell or autoantibody, e.g., an anti-dystonin autoantibody responsible for bullous pemphigoid.

In some embodiments, the cellular membrane is derived from myelin of a nerve or a Schwann cell. Such nanoparticle can target any suitable anti-myelin auto-reactive cell or autoantibody, e.g., an anti-myelin basic protein responsible for multiple sclerosis.

In some embodiments, the cellular membrane is derived from a pancreatic islet cell. Such nanoparticle can target any suitable anti-islet cell auto-reactive cell or autoantibody, e.g., an anti-islet cell responsible for diabetes mellitus.

In some embodiments, the nanoparticle can target an anti-ganglioside autoantibody responsible for Guillain-Barr syndrome. The anti-ganglioside autoantibody can be an anti-GD3 autoantibody, an anti-GM1 autoantibody, an anti-GQ3 autoantibody, or an anti-GT1 autoantibody.

In some embodiments, the cellular membrane is derived from an inner mitochondrial or a bacteria membrane. Such nanoparticle can target any suitable anti-inner mitochondrial or bacteria auto-reactive cell or autoantibody, e.g., an anti-phospholid or anti-cardiolipin autoantibody responsible for antiphospholid syndrome.

In some embodiments, the present methods can be used to treat or prevent immune thrombocytopenia purpura associated with an anti-CD36 and/or an anti-GP IIb-IIIa autoantibody, pemphigus vulgaris associated with an anti-epithelial cadherin protein autoantibody, or multiple sclerosis associated with an anti-myelin protein autoantibody.

The present methods can use any suitable nanoparticle. In some embodiments, the inner core of the nanoparticle can comprise a biocompatible or a synthetic material, such as poly(lactic-co-glycolic acid) (PLGA), polylactic acid (PLA), polyglycolic acid (PGA), polycaprolactone (PCL), polylysine, and polyglutamic acid. In other embodiments, the inner core of the nanoparticle supports the outer surface. The nanoparticle can comprise any suitable cellular membrane derived from a cell or a cellular source, e.g., a red blood cell. For example, the nanoparticle can comprise a plasma membrane or an intracellular membrane derived from a cell, e.g., a red blood cell. In some embodiments, the cellular membrane comprises a plasma membrane derived from a red blood cell, e.g., a plasma membrane derived from a human red blood cell. In some embodiments, the nanoparticle can comprise any suitable naturally occurring cellular membrane derived from a cell, e.g., a red blood cell. In some embodiments, the cellular membrane comprises a naturally occurring plasma membrane derived from a red blood cell, e.g., a naturally occurring plasma membrane derived from a human red blood cell.

The present methods can use a nanoparticle that further comprises a releasable cargo. The nanoparticle can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanoparticle and the subject or by a change of a physical parameter surrounding the nanoparticle. The nanoparticle can comprise any suitable type of releasable cargo. For example, the releasable cargo can be a therapeutic agent, a prophylactic agent, a diagnostic or marker agent, a prognostic agent, or a combination thereof. The therapeutic agent can be a cytotoxic drug capable of cell killing. Any suitable cytotoxic drugs can be used. For example, cytotoxic drugs can be an anthracycline, e.g., doxorubicin or daunorubicin, a taxane, e.g., docetaxel or paclitaxel, or an immunosuppressive agent, e.g., methotrexate or cyclosporin A. In another example, the releasable cargo can be a metallic particle, a polymeric particle, a dendrimer particle, or an inorganic particle or the releasable cargo can be in the form of a metallic particle, a polymeric particle, a dendrimer particle, or an inorganic particle.

In some embodiments, the nanoparticle targets an auto-reactive cell, e.g., an auto-reactive B cell, an auto-reactive T cell, or an auto-reactive lymphocyte. The nanoparticle can further comprise a cytotoxic drug capable of cell killing. Any suitable cytotoxic drugs can be used. For example, cytotoxic drugs can be an anthracycline, e.g., doxorubicin or daunorubicin, a taxane, e.g., docetaxel or paclitaxel, or an immunosuppressive agent, e.g., methotrexate or cyclosporin A. The nanoparticle can comprise a cellular membrane derived from any suitable cell or cellular source, e.g., a cellular membrane derived from a red blood cell, a platelet, an epidermal cell, an epidermal-dermal junction, myelin of a nerve or a Schwann cell, a pancreatic islet cell, a mitochondrial or a bacterium.

The nanoparticle can have any suitable size. For example, the nanoparticle can have a diameter from about 10 nm to about 10 µm. In certain embodiments, the diameter of the nanoparticle is about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm.

The nanoparticle can have any suitable shape, including but not limited to, sphere, square, rectangle, triangle, circular disc, cube-like shape, cube, rectangular parallelepiped (cuboid), cone, cylinder, prism, pyramid, right-angled circular cylinder and other regular or irregular shape.

In some embodiments, the nanoparticle substantially lacks constituents of the cell, e.g., red blood cell, from which the cellular membrane is derived. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell, e.g., red blood cell, from which the cellular membrane is derived. In some embodiments, the nanoparticle comprises a plasma membrane derived from a red blood cell and the nanoparticle substantially lacks hemoglobin. For example, the nanoparticle can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin.

In some embodiments, the nanoparticle substantially maintains the natural structural integrity or activity of the cellular membrane or the constituents of the cellular membrane so that the nanoparticle functions as decoy for the subject's cells, e.g., red blood cells. For example, the nanoparticle can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity for functioning as decoy for the subject's cells, e.g., red blood cells.

In some embodiments, the nanoparticle is biocompatible or biodegradable. For example, the inner core of the nanoparticle may comprise PLGA and the outer surface of the nanoparticle may comprise a plasma membrane derived from a cell, e.g., a red blood cell.

The nanoparticle can have any suitable half-life in vivo. For example, the nanoparticle can have a half-life in blood circulation in vivo for at least about 2-5 times of the half-life of a PEG-coated, comparable nanoparticle, or have a half-life in blood circulation in vivo for at least about 1 to about 40 hours.

The outer surface of the nanoparticle used in the present methods can comprise a synthetic membrane. In some embodiments, the nanoparticles used in the present methods comprise a mixture of nanoparticles that comprise an outer surface comprising a cellular membrane and nanoparticles that comprise an outer surface comprising a synthetic membrane. The nanoparticles that comprise an outer surface comprising a synthetic membrane may or may not comprise a self-antigen that targets an auto-reactive component of an autoimmune disease or condition in a subject. In some embodiments, both the nanoparticles that comprise an outer surface comprising a cellular membrane and nanoparticles that comprise an outer surface comprising a synthetic membrane comprise a self-antigen that targets an auto-reactive component of an autoimmune disease or condition in a subject. In other embodiments, the nanoparticles that comprise an outer surface comprising a cellular membrane comprise a self-antigen that targets an auto-reactive component of an autoimmune disease or condition in a subject, but the nanoparticles that comprise an outer surface comprising a synthetic membrane do not comprise a self-antigen that targets an auto-reactive component of an autoimmune disease or condition in a subject.

The composition used in the present methods can comprise the nanoparticles that comprise an outer surface comprising a cellular membrane and nanoparticles that comprise an outer surface comprising a synthetic membrane in any suitable ratio. In some embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a cellular membrane. In other embodiments, the present composition can comprise at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the nanoparticles that comprise an outer surface comprising a synthetic membrane. For example, the composition used in the present methods can comprise about 1-10% (w/w) of the nanoparticles that comprise an outer surface comprising a cellular membrane and about 90-99% (w/w) of the nanoparticles that comprise an outer surface comprising a synthetic membrane, about 11-25% (w/w) of the nanoparticles that comprise an outer surface comprising a cellular membrane and about 75-89% (w/w) of the nanoparticles that comprise an outer surface comprising a synthetic membrane, about 50% (w/w) of the nanoparticles that comprise an outer surface comprising a cellular membrane and about 50% (w/w) of the nanoparticles that comprise an outer surface comprising a synthetic membrane, about 51-75% (w/w) of the nanoparticles that comprise an outer surface comprising a cellular membrane and about 49-25% (w/w) of the nanoparticles that comprise an outer surface comprising a synthetic membrane, or about 90-100% (w/w) of the nanoparticles that comprise an outer surface comprising a cellular membrane and about 0-10% (w/w) of the nanoparticles that comprise an outer surface comprising a synthetic membrane.

The outer surface of the nanoparticle can comprise a hybrid membrane comprising a cellular membrane derived from a cell and a synthetic membrane. In some embodiments, the outer surface of the nanoparticle can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular membrane. In other embodiments, the outer surface of the nanoparticle can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the nanoparticle can comprise a hybrid membrane comprising about 5-10% (w/w) of a cellular membrane and about 90-95% (w/w) of a synthetic membrane, about 11-25% (w/w) of a cellular membrane and about 75-89% (w/w) of a synthetic membrane, about 50% (w/w) of a cellular membrane and about 50% (w/w) of a synthetic membrane, about 51-75% (w/w) of a cellular membrane and about 49-25% (w/w) of a synthetic membrane, or about 90-99% (w/w) of a cellular membrane and about 1-10% (w/w) of a synthetic membrane.

In some embodiments, the nanoparticle substantially lacks immunogenicity to the subject. For example, the cellular membrane can be derived from a cell, e.g., a red blood cell, from the same species of the subject. In another example, the subject is a human and the cellular membrane is derived from a human cell, e.g., a human red blood cell. In some embodiments, the cellular membrane can be derived from a cell, e.g., a red blood cell, of the subject to be treated. For example, the cellular membrane can be derived from a red blood cell of the human to be treated.

In some embodiments, the present methods can further comprise administering another active ingredient to the subject. The other active ingredient can be used for treating or preventing an autoimmune disease or condition in a subject.

In some embodiments, the present methods can further comprise administering a pharmaceutically acceptable carrier or excipient to the mammal.

The nanoparticle can be administered using any suitable delivery mechanisms or techniques. In some embodiments, the nanoparticle can be administered alone. In other embodiments, the nanoparticle can be administered with a pharmaceutically acceptable carrier or excipient. In still other embodiments, the nanoparticle can be administered via a medicament delivery system.

The present methods can further comprise assessing efficacy of the nanoparticle and/or another active ingredient in treating or preventing an autoimmune disease or condition in a subject. The efficacy of a nanoparticle and/or another active ingredient in an autoimmune disease or condition in a subject can be assessed using any suitable tests. For example, the efficacy of a nanoparticle can be assessed by at least two of the tests, e.g., 2, 3, 4, 5, 6, 7, 8 or 9 of the tests.

The nanoparticle, alone or in combination with other active ingredient(s), can be administered via any suitable administration routes. In some embodiments, the nanoparticle, alone or in combination with other active ingredient(s), can be administered via oral, parenteral, rectal, nasal, topical, or ocular routes, or by inhalation. Exemplary parenteral administration routes include intravenous, intramuscular, intraperitoneal, intranasal, and subcutaneous routes.

In another aspect, the present invention is directed to a use of an effective amount of a nanoparticle for the manufacture of a medicament for treating or preventing an autoimmune disease or condition in a subject, wherein said nanoparticle comprises a) an inner core comprising a non-cellular material, b) an outer surface comprising a cellular membrane comprising a self-antigen that targets an auto-reactive component of said autoimmune disease or condition, and optionally when said cellular membrane is derived from a red blood cell, said medicament is not used for treating or preventing an autoimmune hemolytic disease or condition in said subject. The manufactured medicament can be used to treat or prevent an autoimmune disease or condition in a subject as described above.

In still another aspect, the present invention provides for a combination for treating or preventing an autoimmune disease or condition in a subject, which combination comprises an effective amount of a nanoparticle and an effective amount of a second prophylactic or therapeutic agent for treating or preventing an autoimmune disease or condition in a subject, wherein said nanoparticle comprises a) an inner core comprising a non-cellular material, b) an outer surface comprising a cellular membrane comprising a self-antigen that targets an auto-reactive component of said autoimmune disease or condition, and optionally when said cellular membrane is derived from a red blood cell, said combination is not used for treating or preventing an autoimmune hemolytic disease or condition in said subject. The present invention also provides for a pharmaceutical composition comprising the combination and a method for treating or preventing an autoimmune disease or condition in a subject using the combination or the pharmaceutical composition comprising the combination. The combinations and the pharmaceutical compositions comprising the combinations can be used to treat or prevent an autoimmune disease or condition in a subject as described above.

C. Pharmaceutical Compositions and Administration Routes

The pharmaceutical compositions comprising the nanoparticles, alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanoparticles, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the nanoparticles, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The nanoparticles, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the nanoparticles, alone or in combination with another active ingredient, may be provided in a solid form, such as a tablet or capsule, or as a solution, emulsion, or suspension. To prepare the oral compositions, the nanoparticles, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanoparticles, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the nanoparticles, alone or in combination with other active ingredient(s), may be administered using, for example, a spray formulation also containing a suitable carrier.

For topical applications, the nanoparticles, alone or in combination with other active ingredient(s), are preferably formulated as creams or ointments or a similar vehicle suitable for topical administration. For topical administration, the nanoparticles, alone or in combination with other active ingredient(s), may be mixed with a pharmaceutical carrier at a concentration of about 0.1% to about 10% of drug to vehicle. Another mode of administering the nanoparticles, alone or in combination with other active ingredient(s), may utilize a patch formulation to effect transdermal delivery.

In certain embodiments, the present disclosure provides pharmaceutical composition comprising the nanoparticles, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

One of ordinary skill in the art may modify the formulations within the teachings of the specification to provide numerous formulations for a particular route of administration. In particular, the nanoparticles, alone or in combination with other active ingredient(s), may be modified to render them more soluble in water or other vehicle. It is also well within the ordinary skill of the art to modify the route of administration and dosage regimen of a particular nanoparticle, alone or in combination with other active ingredient(s), in order to manage the pharmacokinetics of the present compounds for maximum beneficial effect in a patient.

D. Exemplary Embodiments

In some embodiments, the present invention provides compositions comprising self-antigen displaying nanoparticles, and methods of use thereof, for targeting auto-reactive immune factors for preventing and/or treating autoimmune diseases. In certain embodiments, the invention provides RBC membrane-cloaked nanoparticle functionalized with RBC antigens to absorb anti-RBC antibodies and prevent their binding to RBCs. The self-antigen displaying nanoparticles of the invention can also be loaded with cytotoxic drugs for targeted cell killing or with immune-tolerizing compounds to normalize the immune regulation.

In some embodiments, the present invention further provides that the inventive nanoparticle comprises a releasable cargo that can be located in any place inside or on the surface of the nanoparticle. In certain embodiments, the releaseable cargo is located within or on the inner core of the inventive nanoparticle. In other embodiments, the releasable cargo is located between the inner core and the outer surface of the inventive nanoparticle. In yet other embodiments, the releasable cargo is located within or on the outer surface of the inventive nanoparticle. A trigger for releasing the releasable cargo from the inventive nanoparticle includes, but is not limited to, a contact between the nanoparticle and a target cell, tissue, organ or subject, or a change of an environmental parameter, such as the pH, ionic condition, temperature, pressure, and other physical or chemical changes, surrounding the nanoparticle.

In certain embodiments, the releasable cargo comprises one or more therapeutic agent, prophylactic agent, diagnostic or marker agent, prognostic agent, or a combination thereof. Examples of therapeutic agents include, but are not limited to, an antibiotic, an antimicrobial, a growth factor, a chemotherapeutic agent, or a combination thereof. Exemplary diagnostic or prognostic agent can be an imaging marker. In yet certain other embodiments, the releasable cargo is a metallic particle comprising a gold particle, a silver particle, or an iron oxide particle. In other embodiments, the releasable cargo is a polymeric particle comprising a poly(lactic-co-glycolic acid) (PCL) particle, a chitosan particle, a hydroxypropyl methacrylamide copolymer (HPMA) particle. In other embodiments, the releasable cargo is a dendrimer particle or an inorganic particle comprising a silica particle, a porous silica particle, a phosphate calcium particle or a quantum dot, or a metallic particle comprising a gold particle, a silver particle, or an iron oxide particle.

In some embodiments, the present invention further provides that the inventive nanoparticle can be in any suitable shape, including, but not limited to, sphere, square, rectangle, triangle, circular disc, cube-like shape, cube, rectangular parallelepiped (cuboid), cone, cylinder, prism, pyramid, right-angled circular cylinder, or other regular or irregular shape, and has a diameter from about 10 nm to about 10 μm. In certain embodiments, the inventive nanoparticle has a diameter from about 50 nm to about 500 nm. In certain embodiments, the nanoparticle of the present invention is biocompatible and/or biodegradable.

In certain embodiments, the nanoparticle of the present invention comprises the cellular plasma membrane derived from a red blood cell and an inner core comprising poly(lactic-co-glycolic acid) (PLGA), wherein the nanoparticle substantially lacks hemoglobin and has a half-life in blood circulation in vivo for at least about 2-5 times the half-life of a nanoparticle having a poly(lactic-co-glycolic acid) (PLGA) inner core coated with polyethylene glycol (PEG). In certain embodiments, such nanoparticle has a half-life in blood circulation in vivo for at least about 5 to about 40 hours.

In some embodiments, the present invention also provides a pharmaceutical composition comprising a medicament delivery system comprising an effective amount of the nanoparticle of the present invention. In certain embodiments, the pharmaceutical composition of the present invention further comprises one or more additional active ingredient, with or without a medically or pharmaceutically acceptable carrier or excipient that can be administered along with or in combination with the nanoparticle of the present invention. The inventive pharmaceutical composition or the medicament delivery system comprising the nanoparticle of the present invention can be administered via any suitable administration route, including but not limited to, oral, nasal, inhalational, parental, intravenous, intraperitoneal, subcutaneous, intramuscular, intradermal, topical, or rectal route.

In certain embodiments, the inventive method is used for treating or preventing autoimmune disease or pathological condition. As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee. In certain embodiments, the cellular membrane of the nanoparticle used for the inventive method is derived from a cell of the same species of the subject. In certain embodiments, the cellular membrane of the nanoparticle used for the inventive method is derived from a red blood cell of the same species of the subject and the red blood cell has the same blood type of the subject. In certain embodiments, the cellular membrane of the nanoparticle used in the inventive method is derived from a cell of the subject.

In some embodiments, the present invention further provides that the inventive methods for treating or preventing an autoimmune disease, disorder, or condition further comprises administering to a subject in need one or more other active ingredient with or without a pharmaceutically acceptable carrier, adjuvant, or excipient, along or in combination with the pharmaceutical composition or medicament delivery system comprising the nanoparticles of the present invention. The inventive methods further provide that the nanoparticle of the present invention is administered to a target site of the subject in need, including but not limited to, a target dermal site, blood or plasma, a target organ, a target tumor site, or target cells, and further provides a mechanism to trigger the release of a releasable cargo at the target site. Mechanisms for triggering the releasable cargo include, but are not limited to, a contact between the nanoparticle of the present invention and a target cell, tissue, organ or subject, or a change of an environmental parameter, such as the pH, ionic condition, temperature, pressure, and other physical or chemical changes, surrounding the nanoparticle of the present invention.

To address a need in immunology and rheumatology, a nanoparticle platform displaying self-antigens to target the auto-reactive components in autoimmune disease was developed. Self-antigen displaying nanoparticles were prepared via a cell membrane cloaking technique, in which cellular membranes and proteins are translocated onto polymeric nanoparticles (FIG. 1). The following studies demonstrate the ability of these nanoparticles to sequester and neutralize autoantibodies. Owing to the cargo loading capacity of the polymeric cores, these biomimetic nanoparticles can also be applied to deliver drugs to selectively deplete B cells and T cells possessing self-antigen receptors. Such scheme can selectively eradicate the pathologic immune components without compromising other immune functions. Furthermore, these biomimetic nanoparticles can be loaded with immune-tolerizing compounds to normalize the immune regulation while also alleviating pathology related to the autoantibody.

Red blood cell (RBC) membrane cloaked nanoparticles were applied to neutralize anti-RBC antibodies, which are the primary auto-reactive immune factor in autoimmune hemolytic anemia (AIHA). AIHA has one the best established pathophysiology regarding autoantibodies, and is a co-autoimmune disease of many of the most common autoimmune diseases (systemic lupus erythema, rheumatoid arthritis, scleroderma, ulcerative colitis) as well as being associated with diseases such as HIV, CLL, and Hodkins lymphoma (4,5). Red blood cell membrane coated poly(lactic-co-glycolic acid) particles approximately 120 nm in size were applied to sequester the auto-antibodies known to cause AIHA. These particles, with red blood cell membrane, are inert particles, but functionally coated with the antigens targeted by warm-agglutinins and anti-RBC IgG in AIHA. Due to beneficial surface area to size ratio that exists between nanoparticles and red blood cells and favorable kinetics of interaction, these nanoparticles are capable of absorbing the auto-antibodies and preventing hemolysis and resultant anemia that typically occurs from this disease.

Several experiments have been carried out to demonstrate that RBC membrane cloaked nanoparticles, which are functionalized with RBC antigens, are able to absorb anti-RBC antibodies and prevent their binding to RBCs. The first experiment was the performance of the direct antibody test (DAT), also called the Coomb's test, which is the clinical gold standard for detecting red blood cell autoantibodies. To do this, nanoparticles coated in mouse red blood membrane were co-incubated with anti-mouse red blood cell antibodies for 1 hour and then a standard Coomb's test was carried out. Results demonstrate that the technology was capable of neutralizing the anti-mouse red blood cell antibody by preventing macroscopic and microscopic agglutination.

To further validate this observation, a second experiment was conducted demonstrating the binding capacity of the membrane coated nanoparticle to absorb antibody. In this experiment, 250 µg of RBC-membrane coated nanoparticles were synthesized with a DiD core for fluorescent detection. Anti-RBC antibody was labeled with fluorescein for its detection. Antibody solution was made in 6 concentrations (500 µg, 250 µg, 125 µg, 31.25 µg, 7.81 µg, 1.95 µg). These 6 solutions were incubated with 250 µg of RBC-membrane coated nanoparticles at 37 C for 1 hour. After 1 hr of incubation, solutions were centrifuged at 14500 rpm for 30 minutes to separate the nanoparticles from the unbound antibody. The supernatant, containing unbound antibody was collected. The pellet was re-suspended in equivalent volume and spun down again to ensure no residual unbound antibody was present. The supernatant solution and the washed nanoparticle solutions were then analyzed for presence of both fluorescein and DiD. Results of the experiment demonstrate that the saturation capacity was approximately 60 µg of antibody per 250 µg of nanoparticles. Specificity between the anti-RBC antibodies and RBC antigen displaying nanoparticles was also demonstrated as a control antibody had lower affinity to the RBC membrane cloaked nanoparticles. In addition, a control nanoparticle functionalized in DSPE-PEG showed lower affinity to the anti-RBC antibodies as compared to the RBC membrane cloaked nanoparticles.

Further in vivo studies were completed demonstrating that administration of the RBC antigen displaying nanoparticles in vivo reduced anemia symptoms upon anti-RBC antibody injections. Together, this data represents a brand new approach using natural, biologically appropriate membrane with self-antigens stabilized by biodegradable polymers to neutralize auto-antibodies and modify disease burden. Detailed descriptions of results and experiments are shown in the following examples.

In addition to targeting auto-reactive immunoglobulin, the self-antigen displaying nanoparticles can be applied to target auto-reactive B cells and T cells. The particles can be loaded with cytotoxic drugs such as cyclosporine, cyclophosphamide, methotrexate and other chemotherapies capable of cell killing. Given that auto-reactive B cells and T cells possess surface receptors that target specific self-antigens, nanoparticles functionalized with these self-antigens will serve as decoy targets for the lymphocytes. In addition, upon binding to the auto-reactive lymphocytes, the nanoparticle can release its cytotoxic payload, thereby achieving selective killing of pathologic lymphocytes. This will selectively and specifically eliminate the B and T-cell populations responsible for disease without broad-spectrum immune suppression.

In certain embodiments, binding of RBC membrane cloaked nanoparticles to anti-glycophorin A hybridoma cells and anti-measles nuclear protein hybridoma cells was compared. The anti-glycophorin A hybridoma cells are known to generate antibodies against glycophorin A, which is a major membrane protein on the surface of RBCs. On the surface of these hybridoma cells are B cell receptors with glycophorin A specificity. On the other hand, anti-measles hybridoma cells are devoid of membrane receptors to RBC antigens. FIG. 2 shows that fluorescently labeled RBC-membrane coated nanoparticles are effective at targeting the Anti-GPA human hybridoma cells as compared to anti-measles hybridoma cells. These studies demonstrate the ability of cell membrane cloaked nanoparticles in targeted auto-reactive cellular immune factors.

In addition to targeting RBC-reactive immune factors, the RBC membrane coated particles may also be applied against anti-ganglioside antibodies, which are implicated in disease pathology of Guillain-Barre syndrome. Gangliosides are present in all cellular membranes and the RBC membrane coated particle is particularly long circulating and a great initial candidate to explore in this disease process.

The present invention is not limited to the RBC membrane cloaked nanoparticles. The approach is expandable as the polymeric core is capable of being coated by a variety of membranes. For instance, nanoparticles can be coated with platelet membrane. Platelet membrane is the target of anti-platelet autoantibodies responsible for the cause of thrombocytopenia in thrombotic thrombocytopenic purpura (TTP) and immune thrombocytopenia purpura (ITP). These particles can be administered to bind anti-platelet antibodies and prevent the activation and destruction of functional platelets, preventing hemorrhage and microthrombi which lead to significant morbidity.

This platform can be further expanded to incorporate other biological membranes on the surface of polymeric or biologically compatible cores to neutralize the antibodies and aberrant cell populations in other diseases. Other disease targets include but are not limited to pemphigus vulgaris (using epidermal cell membrane) (6), myasthenia gravis and multiple sclerosis (myelin membrane) (7), and type 1 diabetes (beta cell membrane) (8). Examples of biological membranes with targeting potential against specific autoimmune diseases can be found in Table 1 below.

TABLE 1

Examples of autoimmune diseases and the targeted cell membranes in these diseases.

| Autoimmune Disease | Auto-Antibody | Location of Antigen |
| --- | --- | --- |
| Idiopathic Thrombocytopenic Purpura | Anti-Platelet | Platelet Membrane |
| Pemphigus Vulgaris | Anti-Desmoglein | Epidermal cell membrane |
| Bullous Pemphigoid | Anti-Dystonin | Epidermal-Dermal junction |
| Multiple Sclerosis | Anti-Myelin Basic Protein | Myelin membrane of nerves, Schwann cells |
| Diabetes Mellitus, Type 1 | Anti-Islet Cell | Pancreatic Islet cell membrane |
| Guillain-Barre Syndrome | Anti-ganglioside | Lipid membranes, Red blood cells |
| Antiphospholipid Syndrome | Anti-phospholipid and anti-Cardiolipin | Inner mitochondrial membrane and many bacteria (E. coli) |

In addition, the invention is not limited to self-antigen displaying nanoparticles prepared via the membrane cloaking technique. Nanoparticles functionalized with individual self-antigen proteins via chemical conjugations and surface adsorptions are also included in the present invention. Self-antigens identified as targets in specific autoimmune diseases can be decorated onto nanoparticle surfaces to target auto-reactive immune factors. Examples of identified self antigens implicated in autoimmune diseases include but are not limited to band-3 and glycophorin proteins in autoimmune hemolytic anemia (9,10), CD36 and GP IIb-IIIa in immune thrombocytopenic purpura (11, 12), epithelial cadherin proteins in pemphigus vulgaris (6), and myelin proteins in multiple sclerosis (7,13).

REFERENCES

1. American Autoimmune Related Diseases Association. *The Cost Burden of Autoimmune Disease: The Latest Front in the War on Healthcare Spending*. 2011.
2. C. Schoen, R. Osborn, S. K. H. How, M. M. Doty, and J. Peugh, *In Chronic Condition: Experiences of Patients with Complex Health Care Needs, in Eight Countries*, 2008, Health Affairs Web Exclusive, Nov. 13, 2008, w1-w16.
3. Peakman, M et al. Optimization of current and future therapy for autoimmune disease. Nat Med. 2012. 18 (1); 59-65.
4. Lee, K. Autoimmune Hemolytic Anemia (AIHA). 2002. UNC School of Medicine. Morning Report Jul. 1, 2002.
5. Karuna, R K. et al. *Clinical Patterns and Hematological Spectrum in Autoimmune Hemolytic Anemia*. J Lab Physicians. 2010; 2 (1):17-20.
6. Amagai, M., V. Klaus-Kovtun, and J. R. Stanley, *Autoantibodies against a novel epithelial cadherin in pemphigus vulgaris, a disease of cell adhesion*. Cell, 1991. 67 (5): p. 869-77.
7. Genain, C. P., et al., *Identification of autoantibodies associated with myelin damage in multiple sclerosis*. Nat Med, 1999. 5 (2): p. 170-5.
8. Vernier, R. L., et al., *Heparan sulfate proteoglycan in the glomerular basement membrane in type* 1 *diabetes mellitus*. Kidney Int, 1992. 41 (4): p. 1070-80.
9. Garratty, G., et al., *Severe autoimmune hemolytic anemia associated with IgM warm autoantibodies directed against determinants on or associated with glycophorin* A. Vox Sang, 1997. 72 (2): p. 124-30.
10. Victoria, E. J., et al., *IgG red blood cell autoantibodies in autoimmune hemolytic anemia bind to epitopes on red blood cell membrane band* 3 *glycoprotein*. J Lab Clin Med, 1990. 115 (1): p. 74-88.
11. Kosugi, S., et al., *Platelet-associated anti-glycoprotein (GP) IIb-IIIa autoantibodies in chronic immune thrombocytopenic purpura mainly recognize cation-dependent conformations: comparison with the epitopes of serum autoantibodies*. Thromb Haemost, 1996. 75 (2): p. 339-45.
12. Schultz, D. R., et al., *Anti-CD*36 *autoantibodies in thrombotic thrombocytopeni purpura and other thrombotic disorders: identification of an* 85 *kD form of CD*36 *as a target antigen*. Br J Haematol, 1998. 103 (3): p. 849-57.
13. Ota, K., et al., *T-cell recognition of an immunodominant myelin basic protein epitope in multiple sclerosis*. Nature, 1990. 346 (6280): p. 183-7.

The present invention is further illustrated by the following exemplary embodiments:

1. A method for treating or preventing an autoimmune disease or condition in a subject in need comprising administering to said subject an effective amount of composition comprising self-antigen displaying nanoparticles to target auto-reactive components of said autoimmune disease or condition.
2. The method of embodiment 1, wherein the subject is a human or a non-human mammal.
3. The method of embodiment 1, wherein said self-antigen displaying nanoparticles are prepared via a cellular membrane cloaking technique or chemical conjugations and surface adsorptions, in which cellular membrane and proteins are translocated onto polymeric nanoparticles.
4. The method of embodiment 3, wherein said cellular membrane is derived from a variety of cells or cellular components selected from the group consisting of red blood cells (RBCs), platelets, epidermal cells, epidermal-dermal junction, myelin of nerves or Schwann cells, pancreatic islet cells, lipids, and inner mitrochondrial and bacteria.
5. The method of embodiment 4, wherein said cellular membrane is derived from RBCs.
6. The method of embodiment 5, wherein the RBC membrane cloaked nanoparticles to sequester and neutralize anti-RBC autoantibodies and reduce anemia symptoms.
7. The method of embodiment 6, wherein the RBC membrane cloaked nanoparticles target to the auto-reactive component selected from the group consisting of auto-reactive immunoglobulin, auto-reactive B cells, auto-reactive T cells, and auto-reactive lymphocytes.
8. The method of embodiment 6, wherein the anti-RBC autoantibody is an anti-glycophorin A (GPA) or anti-ganalioside responsible for Guillain-Barr syndrome.
9. The method of embodiment 4, wherein said cellular membrane is derived from platelets, and wherein the platelet membrane cloaked nanoparticles target anti-platelet autoantibodies responsible for thrombocytopenia, preventing the activation and destruction of functional platelets, hemorrhage and microthrombi in thrombocytopenia purpura.
10. The method of embodiment 4, wherein said cellular membrane is derived from epidermal cells, and wherein said epidermal cell membrane cloaked nanoparticles target anti-desmoglein autoantibodies responsible for pemphigus vulgaris.
11. The method of embodiment 4, wherein said cellular membrane is derived from epidermal-Dermal junction, and wherein said epidermal-dermal junction membrane cloaked nanoparticles target anti-dystonin autoantibodies responsible for bullous pemphigoid.
12. The method of embodiment 4, wherein said cellular membrane is derived from myelin of nerves or Schwann cells, and wherein said myelin membrane cloaked nanoparticles target anti-myelin basic protein responsible for multiple sclerosis.
13. The method of embodiment 4, wherein said cellular membrane is derived from pancreatic islet cells, and wherein said pancreatic islet cell membrane cloaked nanoparticles target anti-islet cells responsible for diabetes mellitus.
14. The method of embodiment 4, wherein said cellular membrane is derived from epidermal-Dermal junction, and wherein said epidermal-dermal junction membrane cloaked nanoparticles target anti-dystonin autoantibodies responsible for bullous pemphigoid.
15. The method of embodiment 4, wherein said cellular membrane is derived from lipids, and wherein said lipid membrane cloaked nanoparticles target anti-ganglioside autoantibodies responsible for Guillain-Barr syndrome.
16. The method of embodiment 4, wherein said cellular membrane is derived from inner mitochondrial or bacteria membranes, and wherein said mitochondrial or bacterial membrane cloaked nanoparticles target anti-phospholid or anti-cardiolipin autoantibodies responsible for antiphospholid syndrome.
17. The method of embodiment 1, wherein said autoimmune disease or condition is selected from the group consisting of band-3 and glycophorin proteins in autoimmune hemolytic anemia, CD36 and GP IIb-IIIa in immune thrombocytopenia purpura, epithelial cadherin proteins in pemphigus vulgaris, and myelin proteins in multiple sclerosis.
18. The method of embodiment 1, wherein said self-antigen displaying nanoparticles further comprise cytotoxic drugs capable of cell killing.
19. The pharmaceutical composition used in any of the method of embodiments 1-18.
20. The medicament delivery system comprising the pharmaceutical composition of embodiment 19.

EXAMPLES

Aspects of the present teachings may be further understood in light of the following examples, which should not be construed as limiting the scope of the present teachings in any way.

Example 1

Clearance of Pathologic Antibodies Using Biomimetic Nanoparticles

Pathologic antibodies have been demonstrated to play a key role in type-II immune hypersensitivity reactions, resulting in the destruction of healthy tissues and leading to considerable morbidity for the patient. Unfortunately, current treatments present significant iatrogenic risk while still falling short for many patients in achieving clinical remission. In the present work the capability of target cell membrane-coated nanoparticles was explored to abrogate the effect of pathologic antibodies in efforts to minimize disease burden, without the need for drug-based immune suppression. Inspired by antibody-driven pathology, intact red blood cell (RBC) membrane stabilized by biodegradable polymeric nanoparticle cores was used to serve as an alternative target for pathologic antibodies in an antibody-induced anemia disease model. Through both in vitro and in vivo studies, efficacy of RBC membrane-cloaked nanoparticles to effectively bind and neutralize anti-RBC polyclonal IgG was demonstrated, and thus circulating RBCs were preserved.

The selective depletion of disease-causing antibodies using nanoparticles offers a new model in the management of type-II immune hypersensitivity reactions. The demonstration of pathophysiological-inspired nanoengineering serves as a valuable prototype for additional therapeutic improvements with the goal of minimizing therapy-related adverse effects. Through the use of cell membrane-cloaked nanoparticles, nanoscale decoys with strong affinity to pathologic antibodies can be administered to disrupt disease processes in a minimally toxic manner. These biomimetic nanoparticles enable indiscriminate absorption of pathologic antibodies regardless of their epitope specificities. The particular approach offers much promise in treating antibody-mediated autoimmune diseases, in which target antigens on susceptible cells can vary from patient to patient.

Introduction

Type-II immune hypersensitivities are driven by pathologic antibodies targeting self-antigens, either naturally occurring or due to exposure to an exogenous substance present on the cellular exterior or extracellular matrix. This disease type makes up many of the most prevalent autoimmune diseases including pernicious anemia, Grave's disease, myasthenia gravis as well as autoimmune hemolytic anemia and immune thrombocytopenia (1-4). In addition, they may occur after the administration of a new drug or following certain infections. Currently, therapies for these immune-mediated diseases remain relatively nonspecific via broad immune suppression (5). For instance, comprehensive immune suppression through systemic glucocorticoids (i.e. prednisone, methylprednisolone), cytotoxic drugs (i.e. cyclophosphamide, methotrexate, azothioprine), and monoclonal antibodies (i.e. rituximab, belimumab, infliximab), dominate treatment regimens to prevent further tissue destruction (6-8). Although this approach to therapy is effective for some patients in achieving remission, its efficacy remains variable and there is a well-established risk of adverse side effects, highlighting the need for better tailored therapies (9, 10).

The development of nanoparticle therapeutics has sparked new hope for the treatment of various important human diseases. Herein, this example demonstrates the application of a biomimetic nanoparticle for the clearance of pathologic antibodies using an established murine model of antibody-induced anemia (11). This disease may be idiopathic, called autoimmune hemolytic anemia (AIHA), or drug induced, called drug-induced anemia (DIA). In both cases, however, auto-antibodies attack surface antigens present on red blood cells (RBCs). Therapy for AIHA is relatively standardized with patients starting on systemic steroids and escalating to cytotoxic drugs and B-cell depleting monoclonal antibodies, and then possibly splenectomy based on patient response to therapy (12, 13). The shortcoming of suppressing the immune system with drug-based therapies is the considerable iatrogenic risk associated with non-specific therapy and heightened susceptibility to severe infections following spleen removal (9, 10, 14). DIA, which can be the result of drug-hapten antibodies or drug-independent auto-antibodies, is treated much the same way with the discontinuance of the offending drug and, much more often than in AIHA, performing blood transfusions (15, 16). A subsequent limitation of repeated transfusions of packed RBCs, is that, although they revive tissue perfusion, they carry the risks of hemolytic transfusion reactions, the formation of alloantibodies, and iron toxicity (17-19).

It has previously been shown that mammalian cellular membrane, from both nucleated and non-nucleated cells, can be fused onto polymeric nanoparticle substrates to form stable core-shell structures (20, 21). These particles have been shown to retain and present natural cell membrane and surface antigens (22), which bare the target epitopes involved in antibody-mediated cellular clearance found in AIHA and DIA. To demonstrate the interception of pathologic antibodies, RBC membrane-cloaked nanoparticles, herein denoted RBC antibody nanosponges (RBC-ANS), were used to serve as alternative targets for anti-RBC antibodies and preserve circulating RBCs (FIGS. 3A-3B). Unlike conventional immune therapy, these biomimetic nanoparticles have no drug payload to suppress normal lymphocytes or immune effector cells. Additionally, unlike blood transfusions, which serve as a replacement therapy, the RBC-ANS serve to deplete circulating antibody levels, without contributing further toxic metabolites due to the hemolysis of transfused cells. Moreover, it has been demonstrated in animal models of autoimmune diseases that the primary target antigens can vary and shift over the course of the diseases (23). Exploiting target cell membranes in their entirety overcomes the varying antigen specificities and presents a novel approach in intercepting the auto-reactive antibody mechanism of type-II immune hypersensitivity reactions.

Results

Figure 4A:
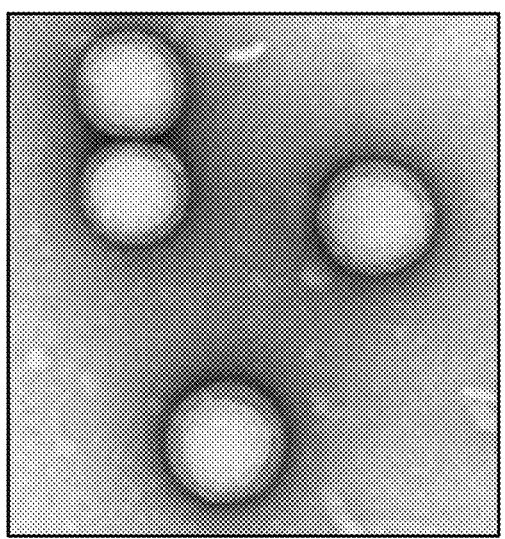
FIGS. 4A-4F. In vitro characterization of RBC-ANS.
Figure 4B:
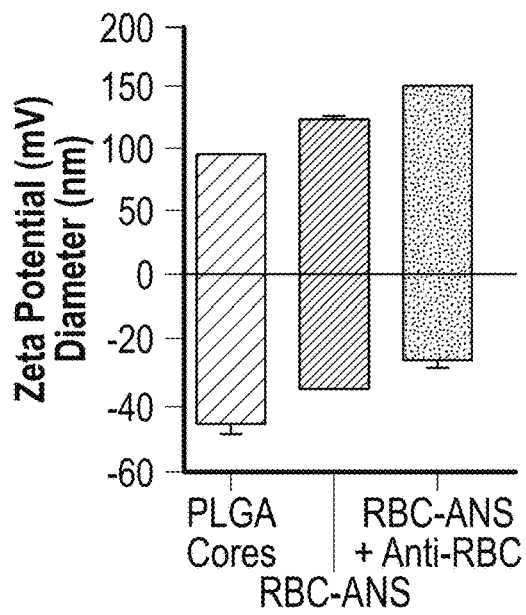
Figure 4C:
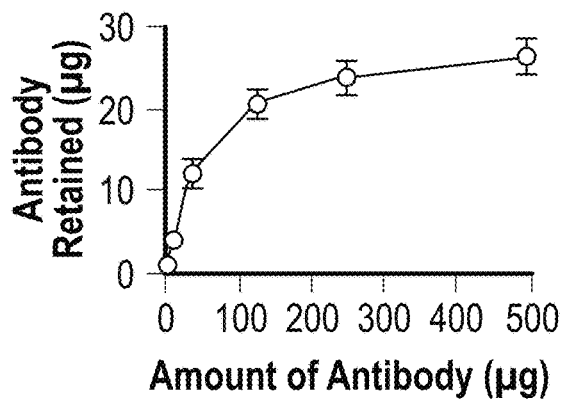
Figure 4D:
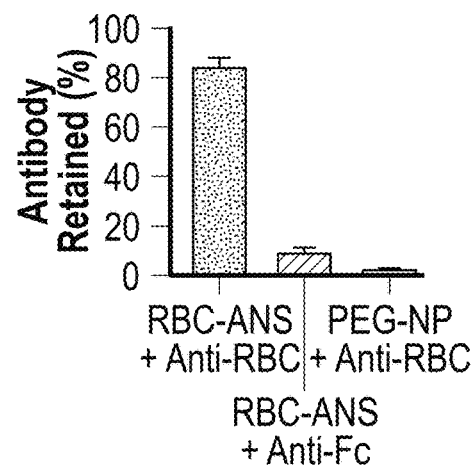
Figure 4E:
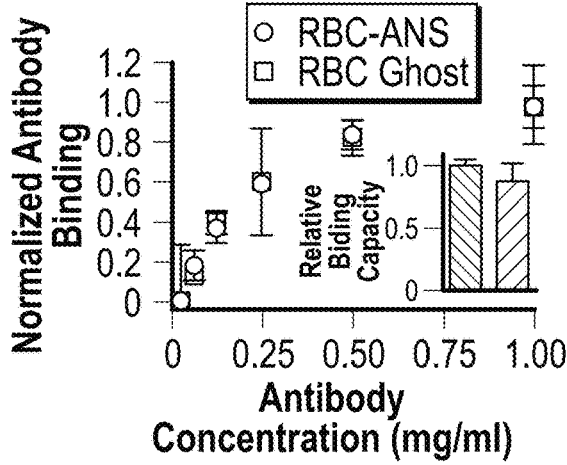
Figure 4F:
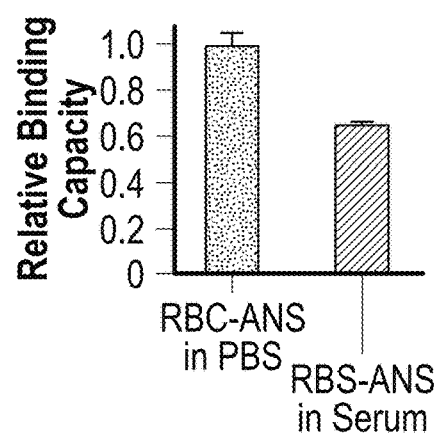

RBC-ANS was constructed following a previously reported protocol (21). in which purified mouse RBC membrane was mechanically extruded with 100 nm poly(lactic-co-glycolic acid) (PLGA) polymeric cores. The resulting nanoparticles revealed a core-shell structure under transmission electron microscopy (TEM) that corresponds to unilamellar membrane coatings over the nanoparticle cores (FIG. 4A). Physicochemical characterizations showed that upon RBC membrane coating, the nanoparticles had a ~20 nm increase in diameter and a 10 mV increase in surface zeta potential (FIG. 4B), which were consistent with addition of RBC membrane to the particle surface (24). Mixture of RBC-ANS with rabbit anti-mouse RBC IgG antibodies (anti-RBC) resulted in a diameter increase of ~26 nm, which can be attributed to the association of the IgG with the RBC-ANS. Such association also resulted in surface charge shielding as was evidenced by the 10 mV increase in the particle zeta potential (FIG. 4B). To better investigate the binding capacity of RBC-ANS for anti-RBC, 250 µg of RBC-ANS was incubated with fluorescently labeled anti-RBC ranging from 1.75 µg to 500 µg. This titration assay demonstrated a plateau in particle-bound antibody fluorescent signal, or binding maximum, corresponding with an antibody mass of ~27 µg yielding a particle-to-antibody mass ratio of approximately 9:1 (FIG. 4C). To evaluate the specificity of antibody-antigen binding, RBC-ANS were incubated with fluorescently labeled anti-RBC or goat anti-mouse Fc IgG (anti-Fc, as a negative control) for 10 min at 37° C. FIG. 4D shows that significantly higher binding signal was observed between RBC-ANS and anti-RBC with very little nonspecific binding with anti-Fc. PEGylated PLGA nanoparticle (PEG-NP) incubated with anti-RBC served as a negative control and showed little retention of the antibody. Furthermore, binding affinity of anti-RBC to RBC-ANS was nearly identical to that of an equivalent amount of RBC ghosts (FIG. 4E). In the presence of serum proteins, RBC-ANS still retained greater than 60% of their anti-RBC binding capacity compared with when the incubation was performed in buffer alone (FIG. 4F). These results are indicative of relatively low nonspecific antibody-nanoparticle binding interactions and demonstrate the necessity for antigen-antibody concordance to achieve neutralization.

Figure 5A:
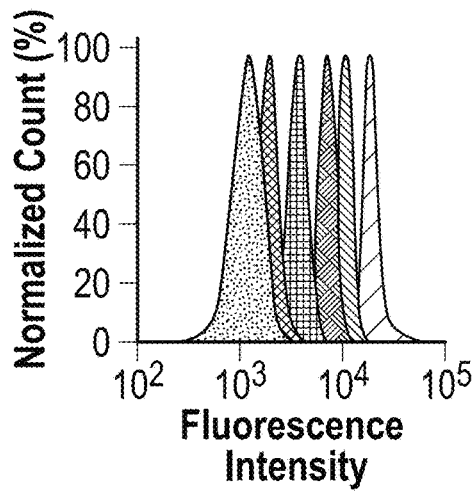
FIGS. 5A-5I. In vitro dose-dependent neutralization and stability of RBC-ANS/anti-RBC binding.
Figure 5B:
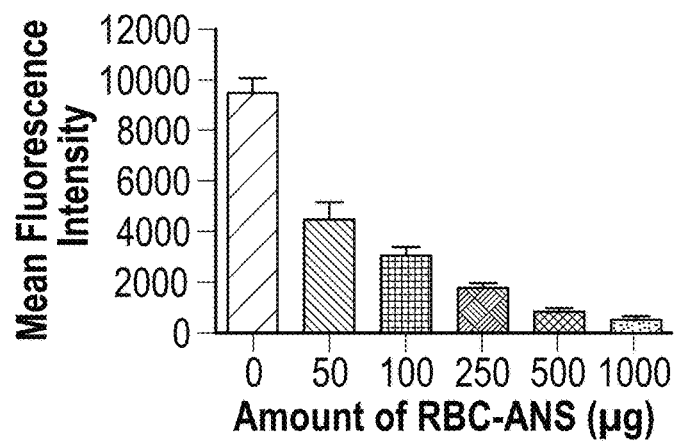
Figure 5C:
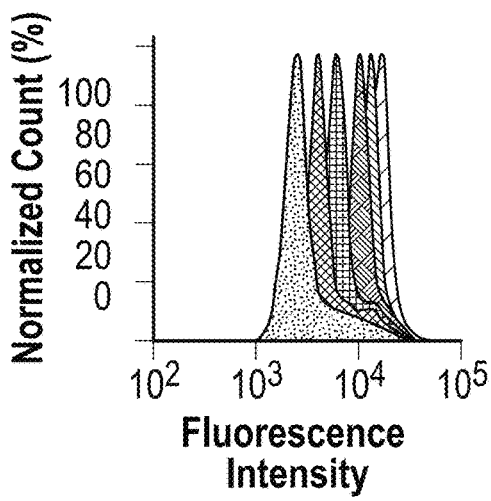
Figure 5D:
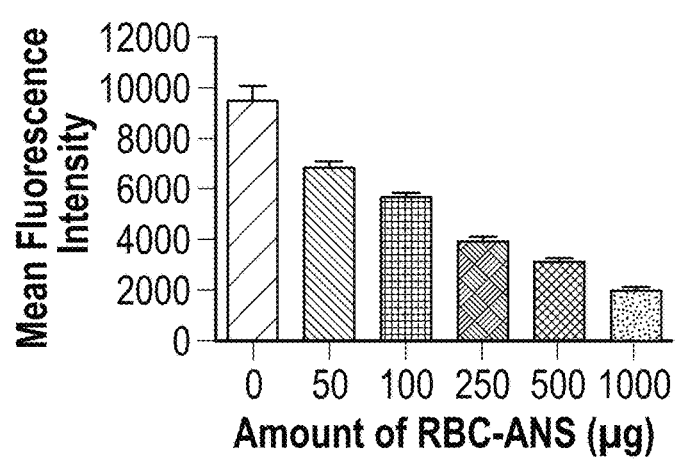
Figure 5E:
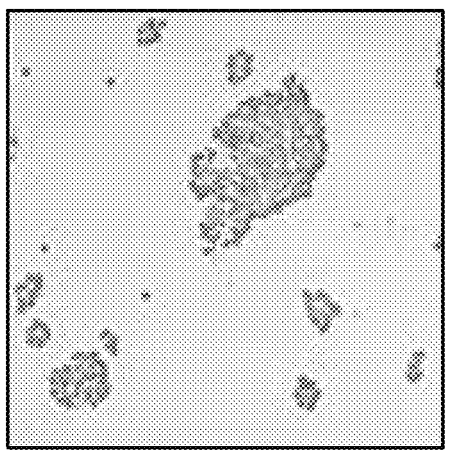
Figure 5F:
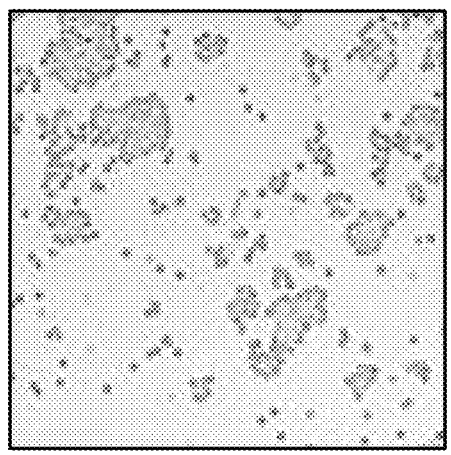
Figure 5G:
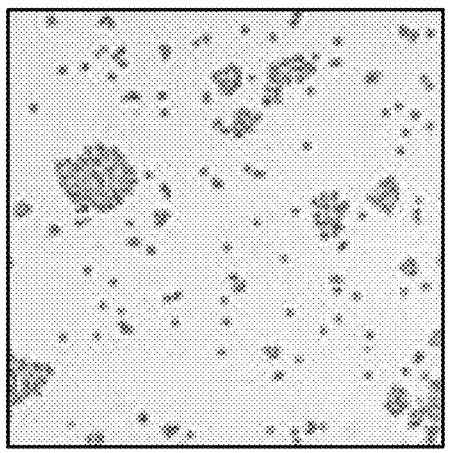
Figure 5H:
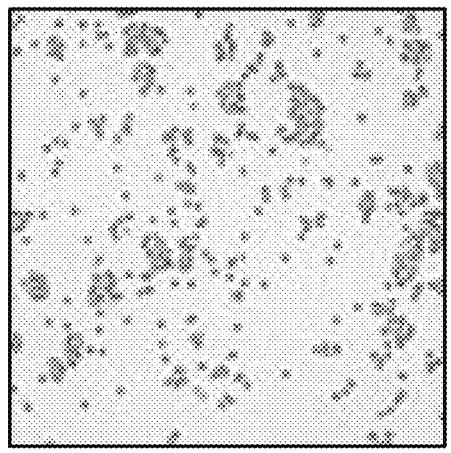
Figure 5I:
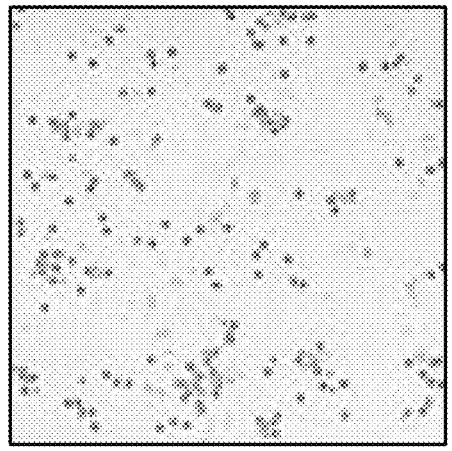

To further characterize the binding stability and competitive binding capacity, the amounts of RBC-ANS mixed with a constant amount of fluorescent anti-RBC in 5% RBC solution were varied. To assess in vitro binding stability, RBC-ANS were pre-incubated with anti-RBC before mixing with 5% RBC solution (FIGS. 5A & 5B) and to test competitive binding capacity, RBC-ANS was added simultaneously with anti-RBC to 5% RBC solution (FIGS. 5C & 5D). After separating the RBCs from any unbound antibodies and RBC-ANS, fluorescent signal associated with the RBCs was measured using flow cytometric analysis. Both pre-incubation and co-incubation studies showed dose-dependent antibody neutralization. High binding ability and stability of RBC-ANS to anti-RBC was shown in the pre-incubation neutralization experiment, which demonstrated a ~60% reduction in RBC-bound antibodies with 100 µg of RBC-ANS and ~95% reduction with 1 mg RBC-ANS as compared to the negative control. Competitive co-incubation showed a reduction of RBC bound antibody signal by ~40% and ~80% at equivalent RBC-ANS doses, respectively. To correlate dose-dependence to clinically relevant diagnostic parameters, an immunoglobulin agglutination test was completed which is equivalent to the qualitative direct antiglobulin test that is a gold standard laboratory diagnostic often used in the diagnoses of AIHA (25, 26). By varying the dose of RBC-ANS from 0 µg to 250 µg a dose-dependent neutralization of anti-RBC (primary antibody) was demonstrated as evidenced by the progressive decrease of RBC agglutination upon addition of an agglutinating secondary antibody (FIGS. 5E to 5I).

Figure 6A:
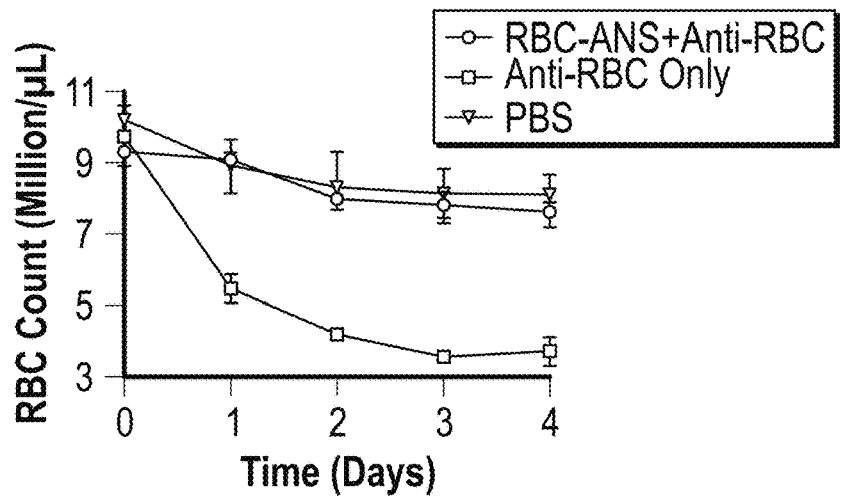
FIGS. 6A-6C. In vivo binding stability of RBC-ANS and anti-RBC. ICR mice (n=6) were intraperitoneally injected with 500 μg of anti-RBC pre-incubated with 5 mg RBC-ANS (red), 500 μg anti-RBC alone (blue) or PBS (black). Blood was collected daily to monitor FIG. 6(A) RBC count (million/μL), FIG. 6(B) hemoglobin (g/dL) and FIG. 6(C) hematocrit (%) of the mice.
Figure 6B:
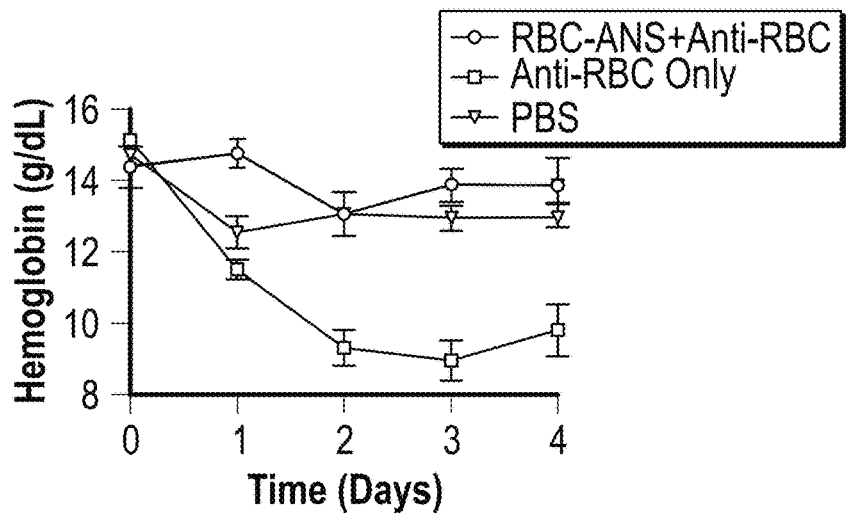
Figure 6C:
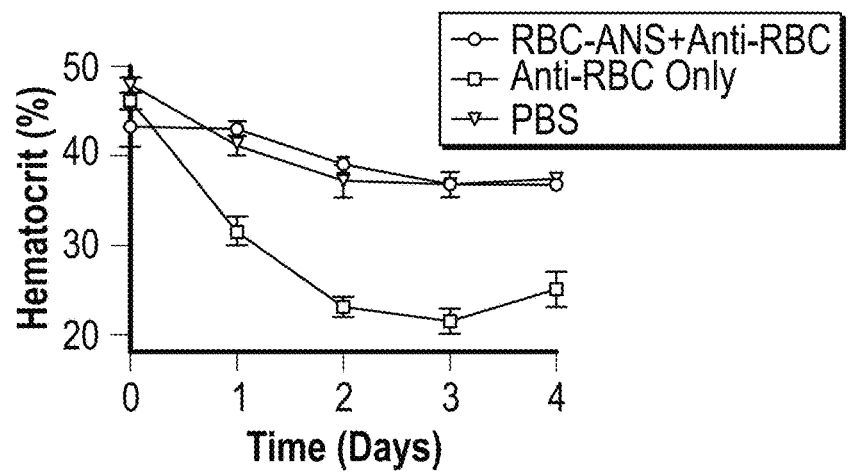

After confirming in vitro that RBC-ANS could selectively bind anti-RBC, the ability of the particles to durably retain antibodies was then assessed in vivo. A previously described anemia disease model, induced through intraperitoneal injection of anti-RBC, was used in the study (11). 500 µg of anti-RBC, a sufficient amount to induce acute anemia, was injected intraperitoneally into mice in the control group. Following the injection, the antibodies could diffuse across the peritoneal membrane, bind to circulating RBCs, and induce their clearance. Mice in the treatment group received the same dose of anti-RBC incubated beforehand for 5 min at 37° C. with 5 mg of RBC-ANS. The relevant clinical parameters used for monitoring anemia responses, including RBC count, hemoglobin level, and hematocrit, of each group were then assessed daily for 4 days. Comparison of the hematological parameters between the control and treatment groups showed that anti-RBC pre-incubated with RBC-ANS was less effective in inducing an anemic response (FIGS. 6A-6C). Mice in the treatment group possessed higher RBC count, hemoglobin content, and hematocrit throughout the duration of the study. All parameters were consistent with control mice that had not been challenged with anti-RBC but had their blood drawn daily. This result suggests that the anti-RBC was trapped by the RBC-ANS and was precluded from binding to circulating RBCs. The experiment demonstrates the feasibility of using target-cell mimicking nanoparticles to neutralize pathologic antibodies.

Figure 7A:
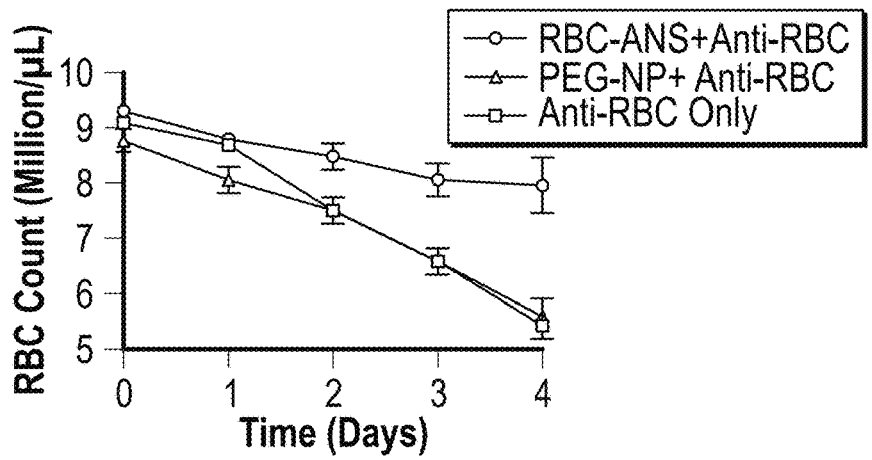
FIGS. 7A-7C. In vivo neutralization of anti-RBC by RBC-ANS. ICR mice (n=10) were intraperitoneally injected with 200 μg anti-RBC on day 0, 1, 2 and 3. After each dose of the antibody, the mice received 2 mg RBC-ANS (red), PEG-NP (black) or PBS (blue) via tail vein intravenous injection. Blood was collected daily to monitor FIG. 7(A) RBC count (million/μL), FIG. 7(B) hemoglobin (g/dL) and FIG. 7(C) hematocrit (%) of the mice.
Figure 7B:
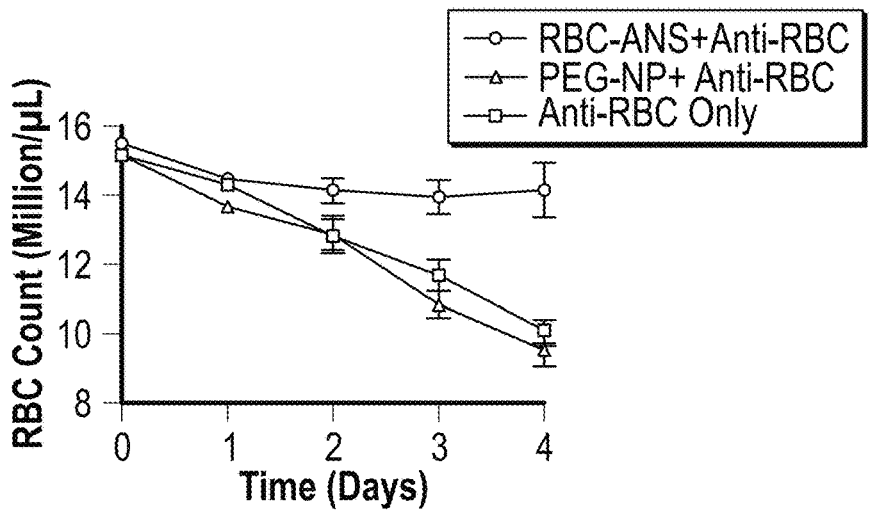
Figure 7C:
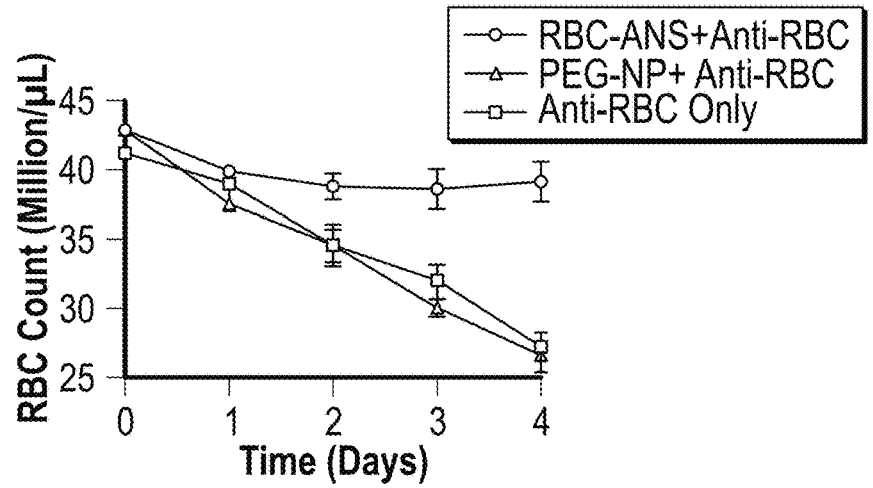
Figure 8:
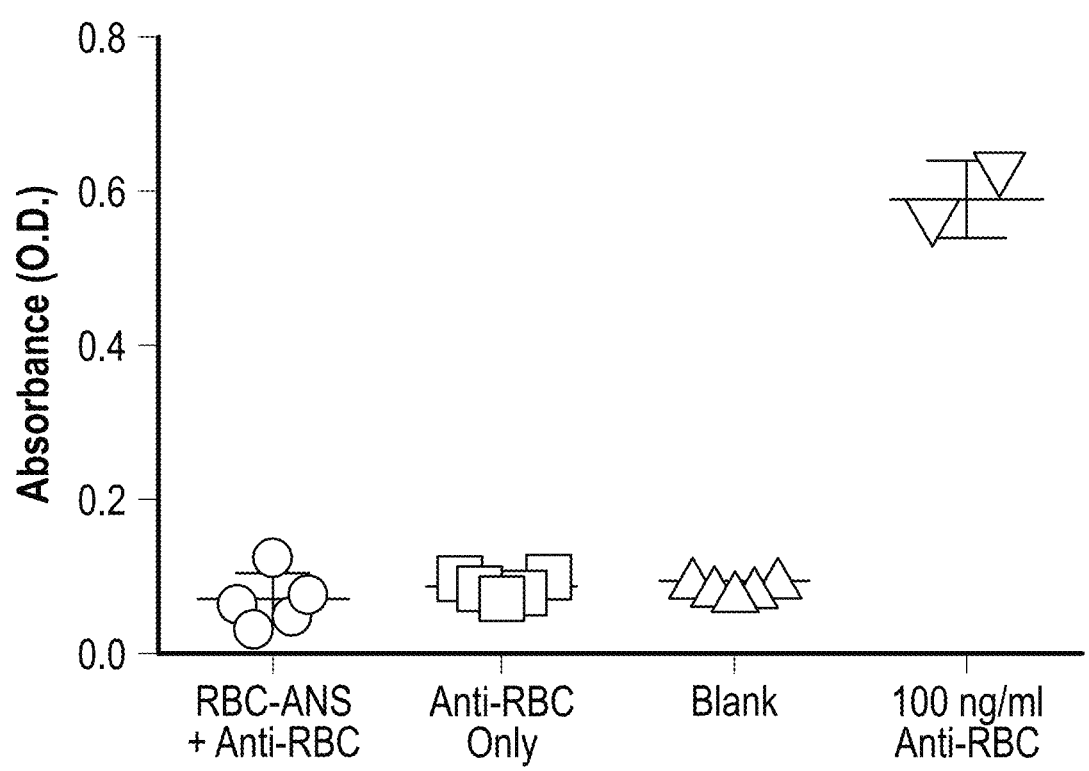
FIG. 8. RBC-ANS do not elicit autoimmune antibodies against RBCs. Six weeks following administration, ELISA analysis of serum from mice receiving RBC-ANS plus anti-RBC, anti-RBC alone, or PBS showed no observable elevation of anti-RBC titer as compared to controls.

To further validate the clinical relevance of the RBC-ANS, low-dose anti-RBC was administered/injected intraperitoneally daily to maintain a sustained level of the antibodies for anemia progression. RBC-ANS was injected intravenously with the aim of neutralizing the circulating antibodies and retarding anemia development. PEG-NPs of analogous size were also administered as a control. Mice were divided into RBC-ANS plus anti-RBC, PEG-NP plus anti-RBC, and PBS plus anti-RBC groups. All mice received 100 µg of anti-RBC daily, through intraperitoneal injection, followed by an intravenous injection of 2 mg of either RBC-ANS, PEG-NP, or PBS daily for 4 days. Blood was obtained daily for the duration of the experiment to assess RBC count, hemoglobin and hematocrit. Starting from day 2, significant benefit in anemia related parameters was observed in the RBC-ANS-treated group as compared to PEG-NP control mice and vehicle only mice (FIGS. 7A-7C). The inability for PEG-NP to prevent anemia further supports the antigen-specific clearance of anti-RBC mediated by RBC-ANS as opposed to the preservation of RBCs via saturation of the mononuclear phagocyte system (27, 28). To further assess the safety of the RBC-ANS approach, the autologous anti-RBC serum titers was also examined in mice 6 weeks following RBC-ANS treatment. ELISA assessment of autoantibodies against mouse RBCs showed no observable elevation of autologous anti-RBC responses in mice receiving RBC-ANS treatment as compared to the controls. The result confirms that the RBC-ANS/anti-RBC complex does not potentiate a humoral immune response against particle associated membrane antigens (FIG. 8).

Discussion

Autoimmune diseases, which include type-II, type-III, and type-IV immune hypersensitivity reactions, are known to attack almost every body tissue, make up over 50 diseases, and contribute to over $65 billion in healthcare costs annually (29). AIHA was attributed to an autoantibody in 1904 by Donath and Landsteiner and the mechanism of extravascular hemolysis described by Metchinkoff in 1905, making it the first disease known to be caused by this mechanism (30). Although the etiology is often idiopathic, it can be induced by drugs (cephalosporins, chemotherapies, quinines) as well as malignancies and viral infections (25, 26, 30). Despite the differences in etiology, the final common disease pathway is the generation of antibodies against RBC membrane components, typically rhesus group and glycophorins, by a B-lymphocyte population that has lost self-tolerance to RBC surface-antigen(s) (31). Most commonly, the pathologic mechanism is IgG-mediated attack that leads to the opsonization of RBCs for extravascular destruction by phagocytes. Alternatively, AIHA can also be induced by IgM-mediated attack on RBCs, which causes RBC intravascular hemolysis via activation of the complement system (26, 30, 32, 33). Even though autoantibodies have long been recognized to play a significant role in the disease, to our knowledge, therapies specifically directed at these pathologic antibodies were not previously explored. Existing AIHA therapy continues to target upstream disease mechanisms through reliance on broad immune suppression, blood transfusions, or splenectomy for refractory cases (12, 15). This treatment paradigm holds true for other type-II immune hypersensitivities which are also managed with broad immune suppression such as using systemic glucocorticoids or cytotoxic drugs (3, 34).

Although efficacious for many patients, systemic steroids carry some of the highest risks of iatrogenic illness. Adverse effects of therapy include steroid myopathy, nosocomial infection, aseptic bone necrosis, accelerated osteoporosis, weight gain, metabolic derangements and Cushinoid appearance (35, 36). In addition to these side effects, if steroid therapy fails, a patient may need to undergo surgery or systemic B-cell depletion with monoclonal antibodies or cytotoxic drugs with side effects of severe infection, antibody transfusion reactions and even the development of malignancies (10, 37). Given this landscape, it is meaningful to continue development of innovative therapeutic strategies to manage disease burden while minimizing iatrogenic risk. Nanoparticles have already shown promise in reducing the risk of systemic toxicity of chemotherapy while increasing efficacy both in emerging literature and clinically (38-40). This example demonstrated that nanoparticles can be engineered to intercept binding between pathologic antibodies and their target cells to favorably impact disease status. The particular approach offers a novel therapeutic intervention for type-II immune hypersensitivity reactions by targeting a final pathologic mechanism and presents an attractive alternative to broad-spectrum immune suppression.

Through the stabilization of biological membrane on a polymeric nanoparticle substrate, it was unveiled the ability of cell membrane-coated nanoparticles to favorably serve as an antibody-decoy to improve disease parameters. The results indicate the ability of RBC-ANS to effectively bind to anti-RBC and preclude their interaction with RBCs. The therapeutic potential of the proposed approach was validated in vivo with separate administrations of anti-RBC and RBC-ANS via intraperitoneal and intravenous route respectively. While the RBC-ANS reduced the antibody-mediated anemic response, equivalent doses of PEG-NP of analogous physicochemical properties failed to moderate the effect of the anti-RBC. The outcome of the in vivo study further indicates that the improved hematological status upon RBC-ANS treatment was mediated by specific antibody-antigen interaction, rather than particle-mediated saturation of phagocytic cells (27, 28). It was also established a lack of humoral response against the RBC membrane antigens following administrations of RBC-ANS and anti-RBC, which validates the safety of the approach as the RBC-ANS, in the presence of anti-RBC, did not potentiate an RBC autoantibody immune response. It has been previously reported that RBC membrane-coated nanoparticles are primarily metabolized in the liver (21, 41), where particulate metabolism generally promotes a tolerogenic immune response (42, 43). In addition, several reports have shown that antigen-laden polymeric nanoparticles, in the absence of immune adjuvants, are also immune-tolerizing (44-46). While rigorous immunological studies in more faithful AIHA animal models are warranted, the present study exhibits the feasibility of applying cell membrane-coated nanoparticles for clearing pathologic antibodies. Adding promise to the approach is the demonstration of both nucleated and non-nucleated mammalian cell membranes that have been successfully stabilized by nanoparticle cores (20, 21). This capacity to functionalize particles, with a variety of multi-antigen membranes, offers a new platform for the development of a robust line of therapies against additional type-II immune hypersensitivities.

Currently, the paradigm in targeted nanomedicine revolves around high-throughput screening for ligand-receptor recognition and the subsequent nanoparticle functionalization with specific targeting molecules (47, 48). With regards to type-II immune hypersensitivity reactions, such a functionalization process could prove limited owing to the varying antigen specificities among pathologic antibodies from patient to patient such as in the case of AIHA (11, 23, 45). Through the appropriate application of biological membranes, which possess the diversity of surface antigens susceptible to pathologic antibodies, biomimetic nanoparticles can be prepared in a facile manner for selective immunomodulation. Furthermore, drug-loaded cores or those made from different materials, such as metallic or inorganic nanoparticles, can be employed to create multifunctional formulations. The demonstration of pathophysiological-inspired nanoengineering serves as a valuable prototype for additional therapeutic advances, offering the opportunity for selective disease intervention while minimizing iatrogenic risks associated with many traditional drug-based therapies.

Example 2

Materials and Methods

Preparation of RBC Antibody Nanosponges (RBC-ANS). RBC-ANS were prepared following previously described methods (21). Briefly, ~100 nm PLGA polymeric cores were prepared using 0.67dL/g carboxy-terminated 50:50 poly(DL-lactide-co-glycolide) (LACTEL Absorbable Polymers, Cupertino, CA) in a nanoprecipitation process. The PLGA polymer was first dissolved in acetone at a 10 mg/mL concentration. 1 mL of the solution was then added rapidly to 3 mL of water. For fluorescently labeled formulations, 1,1'-dioctadecyl-3,3,3',3'-tetramethylindodicarbocyanine perchlorate (DiD, excitation/emission=644/665 nm, Life Technologies) was loaded into the polymeric cores at 0.1 wt %. The mixture was then stirred in open air for 1 hr and placed in vacuum for another 3 hr. The resulting nanoparticle solution was filtered using Amicon Ultra-4 Centrifugal Filters with a molecular weight cutoff of 10 kDa (Millipore, Billerica, MA). RBC membrane coating was then completed by fusing RBC membrane vesicles with PLGA particles via sonication using an FS30D bath sonicator at a frequency of 42 kHz and a power of 100 W for 2 min. The size and the zeta potential of the resulting RBC-ANS were obtained from three dynamic light scattering (DLS) measurements using a Malvern ZEN 3600 Zetasizer, which showed an average hydrodynamic diameter of ~100 and ~115 nm before and after the membrane coating process, respectively. The structure of RBC-ANS was examined with transmission electron microscopy (TEM). A drop of the RBC-ANS solution at 100 g/mL was deposited onto a glow-discharged carbon-coated grid for 10 sec and then rinsed with 10 drops of distilled water. A drop of 1 wt % uranyl acetate stain was added to the grid. The sample was then imaged using an FEI 200 kV Sphera microscope. PEGylated PLGA nanoparticle (PEG-NP) was prepared using poly(ethylene glyocol) methyl ether-block-poly(lactide-co-glycolide) (PEG-PLGA) (Sigma Aldrich, St. Louis, MO). The PEG-PLGA polymer was dissolved in acetone at 10 mg/mL and 1 mL solution was added to 3 mL of water. For fluorescently labeled formulations, DiD was loaded into the polymeric cores at 0.1 wt %. The mixture was then stirred in open air for 1 hr and subsequently placed in vacuum for another 3 hr.

RBC-ANS Binding Capacity and Specificity Studies. Antibodies were first labeled with fluorescein isothiocyanate (FITC). Specifically, 100 µL of polyclonal rabbit anti-mouse RBC IgG (anti-RBC) (Rockland Antibodies and Assays, Gilbertsville, PA) at 10 mg/mL was mixed with 3.0 µL of 10 mg/mL FITC (Thermo Scientific, Rockford, IL) in dimethyl sulfoxide (DMSO). The mixture was incubated at room temperature in the dark for 1 hr and then run through a SEPHADEX G-25 column (Sigma-Aldrich, St. Louis, MO) with de-ionized water to purify conjugated FITC-anti-RBC for subsequent experiments. For the antibody retention study, 250 µg of DiD-loaded RBC-ANS were combined with 6 serial dilutions (500 µg, 250 µg, 125 µg, 31.25 µg, 7.81 µg, 1.95 µg) of FITC-labeled antibody in triplicate in a COSTAR 96 well plate (Corning Unlimited, Corning, NY). Prior to incubation, the samples' fluorescence intensities were measured using a Tecan INFINITE M200 reader (TeCan, Switzerland) to determine 100% signal of FITC (515 nm) and DiD (670 nm). Solutions were then incubated for 30 min at 37° C., followed by spinning down in a Legend 21R Microcentrifuge (Thermo Scientific, Rockford, IL) at 21,200 RPM for 5 min to collect pelleted RBC-ANS/anti-RBC complex. Samples were then washed 3 times in 1 mL water and their fluorescence intensity was re-measured to determine signal intensity of FITC in relation to DiD. All DiD signals were greater than 90% original ensuring minimal loss during washing steps. These steps were repeated at optimum concentrations of 250 µg DiD-loaded RBC-ANS or 250 µg DiD-loaded PEG-NP combined with 7.8 µg FITC-anti-RBC and 7.8 µg FITC-conjugated goat anti-mouse Fc IgG (anti-Fc) (Rockland Antibodies and Assays, Gilbertsville, PA) to determine specificity of RBC-ANS against anti-RBC as compared to control samples. To compare binding kinetics, serially diluted concentrations of FITC-anti-RBC (1, 0.5 0.25, 0.125, 0.063 and 0.031 mg/mL) were incubated with a constant substrate concentration (0.25 mg/mL RBC-ANS or equivalent amount of RBC ghosts). Final values were normalized to the maximum binding observed at saturation. Binding capacity was expressed as a ratio of the fluorescent signals at saturation. To test binding capacity in serum, RBC-ANS was incubated with a saturated amount of FITC-anti-RBC in PBS or in the presence of 50 vol % fetal bovine serum (Thermo Scientific, Rockford, IL). Values were expressed as a ratio of the fluorescent signals.

Competitive Binding Studies. RBC-ANS were prepared at 1 mg/mL in 1×Dulbecco's phosphate buffered saline (PBS) (GIBCO, Grand Island, NY) and serially diluted to make 5 solutions (1 mg/mL, 500 µg/mL, 250 µg/mL, 100 µg/mL, 50 g/mL) with 1×PBS as control. For the pre-incubation study, these solutions were combined with 50 µg anti-RBC and incubated for 2 min at 37° C. before the addition of 1 mL of washed 5% mouse RBC solution. For the competitive co-incubation study, RBC-ANS and anti-RBC were added simultaneously to 1 mL of 5% RBC solution. Each experiment was done in triplicate. Samples were allowed to incubate for 10 min at 37° C. and then washed three times in 1×PBS to thoroughly remove supernatant and collect RBC pellet. Flow cytometry was used to measure the FITC signal of the collected RBC population using a Becton Dickinson FACSCanto II. Flow cytometry data was analyzed using Flowjo software from Treestar.

RBC Agglutination Titration. The experiment was carried out per manufacturer (Rockport Antibodies and Assays) instructions. Briefly, 100 µL of anti-RBC (primary antibody) at 156 µg/mL was added to 100 µL of 5% washed RBC in 1×PBS along with 62.5 µL of RBC-ANS (250 µg, 100 µg, 50 µg, 25 µg or 0 µg) and incubated for 45 min at 37° C. The RBC solution was then washed three times by centrifuging the sample at 3,500 rpm for 1 min and exchanging the supernatant with 1×PBS each time. 100 µL of anti-Fc (agglutinating secondary antibody) at 156 µg/mL was added to each sample, which was vortexed at 625 rpm for 5 min and then spun down at 3,500 rpm for 20 sec. The sample was then re-suspended using a pipette to disrupt the pellet. For the negative control, 100 µL of 6% BSA was used in lieu of secondary antibody. All samples were then viewed via light microscope at 10× magnification and imaged via mounted camera.

In vivo stability of RBC-ANS and anti-RBC binding. Following induction of anemia via intraperitoneal injection of anti-RBC, we randomly assorted 12 ICR mice into two groups of 6. Treatment group received 500 µg anti-RBC incubated with 5 mg RBC-ANS for 5 min at 37° C. prior to injection and anti-RBC only mice received anti-RBC incubated in 1×PBS for 5 min. A control group of mice received injections of PBS only. A few drops of blood were collected from each mouse prior to injections on day 0 to establish starting blood counts and repeated on each day of the experiment. Samples were stored in Potassium-EDTA MICROVETTE tubes (Sarstedt, Newton, NC) and vigorously mixed to prevent clotting. Samples were then run the same day in a Drew Scientific Hemavet 950 (ERBA Diagnostics, Waterbury, CT) and RBC count, hemoglobin and hematocrit were recorded daily.

In vivo neutralization of circulating anti-RBC by RBC-ANS. Using the established intraperitoneal model for antibody delivery, 30 mice were randomized to three groups of 10. Each group of mice received a 100 µl intraperitoneal injection of 2 mg/mL anti-RBC on days 0, 1, 2 and 3. The treatment group also received a tail vein intravenous injection of 200 µL of RBC-ANS (10 mg/mL) in 1×PBS within 30 min of intraperitoneal antibody delivery. The PEG-NP group received an equivalent intravenous dose of PEG-NP and the anti-RBC only group received 200 µL PBS via intravenous injection. RBC count, hemoglobin and hematocrit of each sample were recorded on days 0, 1, 2, 3, and 4.

Anti-RBC Autoimmune Study. Six weeks after the in vivo neutralization studies, serum was collected from 12 mice, 6 in each group, and a standard ELISA was performed. Washed ICR mouse RBCs were plated at 1×10⁶ RBCs per well onto a COSTAR 96 well plate. 100 µL of collected serum was added in a sequence of six 1:5 dilutions. Horseradish peroxidase-conjugated goat anti-mouse antibody IgG (Biolegend, San Diego, CA) was used to probe for bound antibodies. The plate was developed using TMB (3,3',5,5'-tetramethylbenzidine) substrate and 1 M HCl was used to stop the reaction. Absorbance was measured at 450 nm.

REFERENCES

1. Jacobson D L, Gange S J, Rose N R, & Graham N M H (1997) Epidemiology and estimated population burden of selected autoimmune diseases in the United States. *Clin Immunol Immunop* 84 (3):223-243.
2. Wakayama H, et al. (2000) Abolition of anti-glomerular basement membrane antibody-mediated glomerulonephritis in FcR gamma-deficient mice. *Eur J Immunol* 30(4):1182-1190.
3. Hudson B G, Tryggvason K, Sundaramoorthy M, & Neilson E G (2003) Alport's syndrome, Goodpasture's syndrome, and type IV collagen. *New Engl J Med* 348 (25):2543-2556.
4. Weetman A P (2000) Medical progress: Graves' disease. *New Engl J Med* 343(17):1236-1248.
5. Edwards J C W & Cambridge G (2006) B-cell targeting in rheumatoid arthritis and other autoimmune diseases. *Nat Rev Immunol* 6(5):394-403.
6. Wallace D J, et al. (2009) A Phase II, randomized, double-blind, placebo-controlled, dose-ranging study of belimumab in patients with active systemic lupus erythematosus. *Arthrit Rheum-Arthr* 61(9):1168-1178.
7. Worlledge S M B M, Cooper A C, Hobbs J R, & Dacie J V (1968) Immunosuppressive drugs in treatment of autoimmune haemolytic anaemia. *P Roy Soc Med* 61(12): 1312-1315.
8. Emilia G, Messora C, Longo G, & Bertesi M (1996) Long-term salvage treatment by cyclosporin in refractory autoimmune haematological disorders. *Brit J Haematol* 93(2):341-344.
9. Tabas I & Glass C K (2013) Anti-inflammatory therapy in chronic disease: Challenges and opportunities. *Science* 339(6116):166-172.
10. Hansel T T, Kropshofer H, Singer T, Mitchell J A, & George A J T (2010) The safety and side effects of monoclonal antibodies. *Nat Rev Drug Discov* 9(4):325-338.
11. Meyer D, et al. (1998) Fc gamma RIII (CD16)-deficient mice show IgG isotype-dependent protection to experimental autoimmune hemolytic anemia. *Blood* 92(11): 3997-4002.
12. Lechner K & Jager U (2010) How I treat autoimmune hemolytic anemias in adults. *Blood* 116(11):1831-1838.
13. Arnold D M, et al. (2012) A pilot randomized trial of adjuvant rituximab or placebo for nonsplenectomized patients with immune thrombocytopenia. *Blood* 119(6): 1356-1362.
14. Kyaw M H, et al. (2006) Evaluation of severe infection and survival after splenectomy. *Am J Med* 119(3): 276e271-276e277.
15. Crowther M, et al. (2011) Evidence-based focused review of the treatment of idiopathic warm immune hemolytic anemia in adults. *Blood* 118(15):4036-4040.
16. Petz L D (2004) A physician's guide to transfusion in autoimmune haemolytic anaemia. *Brit J Haematol* 124 (6):712-716.
17. Salama A, Berghofer H, & Muellereckhardt C (1992) Red-blood-cell transfusion in warm-type autoimmune hemolytic-anemia. *Lancet* 340(8834-5):1515-1517.
18. Ahrens N, Pruss A, Kahne A, Kiesewetter H, & Salama A (2007) Coexistence of autoantibodies and alloantibodies to red blood cells due to blood transfusion. *Transfusion* 47(5):813-816.
19. Shander A, Cappellini M D, & Goodnough L T (2009) Iron overload and toxicity: the hidden risk of multiple blood transfusions. *Vox Sanguinis* 97(3):185-197.
20. Fang R H, et al. (2014) Cancer cell membrane-coated nanoparticles for anticancer vaccination and drug delivery. *Nano Lett* 14(4):2181-2188.
21. Hu C M J, et al. (2011) Erythrocyte membrane-camouflaged polymeric nanoparticles as a biomimetic delivery platform. *Proc Natl Acad Sci USA* 108(27):10980-10985.
22. Hu C M J, et al. (2013) 'Marker-of-self' functionalization of nanoscale particles through a top-down cellular membrane coating approach. *Nanoscale* 5(7):2664-2668.
23. Hall A M, et al. (2007) Deletion of the dominant autoantigen in NZB mice with autoimmune hemolytic anemia: effects on autoantibody and T-helper responses. *Blood* 110(13):4511-4517.
24. Hochmuth R M, Evans E A, Wiles H C, & Mccown J T (1983) Mechanical measurement of red-cell membrane thickness. *Science* 220(4592):101-102.
25. Bass G F, Tuscano E T, & Tuscano J M (2014) Diagnosis and classification of autoimmune hemolytic anemia. *Autoimmun Rev* 13(4-5):560-564.
26. Packman C H (2008) Hemolytic anemia due to warm autoantibodies. *Blood Rev* 22(1):17-31.
27. Crow A R, Song S, Semple J W, Freedman J, & Lazarus A H (2001) IVIg inhibits reticuloendothelial system function and ameliorates murine passive-immune thrombocytopenia independent of anti-idiotype reactivity. *Brit J Haematol* 115(3):679-686.
28. Samuelsson A, Towers T L, & Ravetch J V (2001) Anti-inflammatory activity of IVIG mediated through the inhibitory Fc receptor. *Science* 291(5503):484-486.
29. Persidis A (1999) Autoimmune disease drug discovery. *Nat Biotech* 17(10):1038-1039.
30. Mack P, & Freedman J (2000) Autoimmune hemolytic anemia: A history. *Transfus Med Rev* 14(3):223-233.
31. Leddy J P, et al. (1994) Erythrocyte-cembrane proteins reactive with IgG (warm-reacting) anti-red blood-cell autoantibodies: II. antibodies coprecipitating band-3 and glycophorin-A. *Blood* 84(2):650-656.
32. Konig A L, Kather H, & Roelcke D (1984) Autoimmune hemolytic-anemia by coexisting anti-I and Anti-Fl cold agglutinins. *Blut* 49(5):363-368.
33. Semple J W & Freedman J (2005) Autoimmune pathogenesis and autoimmune hemolytic anemia. *Semin Hematol* 42(3):122-130.
34. Daniel B S, Borradori L, Hall R P, & Murrell D F (2011) Evidence-based management of bullous pemphigoid. *Dermatol Clin* 29(4):613-620.

35. Buttgereit F, Burmester G R, Straub R H, Seibel M J, & Zhou H (2011) Exogenous and Endogenous Glucocorticoids in Rheumatic Diseases. *Arthritis Rheum-US* 63(1): 1-9.
36. Saag K G, Caldwell J R, Brasington R, & Furst D E (1995) Serious adverse events with low-dose, long-term corticosteroid-therapy in rheumatoid-arthritis—Reply. *Am J Med* 99(6):693-694.
37. Lenz H J (2007) Management and preparedness for infusion and hypersensitivity reactions. *Oncologist* 12(5): 601-609.
38. Karve S, et al. (2012) Revival of the abandoned therapeutic wortmannin by nanoparticle drug delivery. *Proc Natl Acad Sci USA* 109(21):8230-8235.
39. Green M R, et al. (2006) Abraxane (®), a novel Cremophor (®)-free, albumin-bound particle form of paclitaxel for the treatment of advanced non-small-cell lung cancer. *Ann Oncol* 17(8):1263-1268.
40. O'Byrne K J, et al. (2002) A phase I dose-escalating study of DaunoXome, liposomal daunorubicin, in metastatic breast cancer. *Brit J Cancer* 87(1):15-20.
41. Hu C M J, Fang R H, Copp J, Luk B T, & Zhang L (2013) A biomimetic nanosponge that absorbs pore-forming toxins. *Nat Nanotechnol* 8(5):336-340.
42. Crispe I N (2003) Hepatic T cells and liver tolerance. *Nat Rev Immunol* 3(1):51-62.
43. Klugewitz K, et al. (2002) Immunomodulatory effects of the liver: Deletion of activated CD4 (+) effector cells and suppression of IFN-gamma-producing cells after intravenous protein immunization. *J Immunol* 169(5):2407-2413.
44. Basarkar A & Singh J (2009) Poly(lactide-co-glycolide)-polymethacrylate nanoparticles for intramuscular delivery of plasmid encoding interleukin-10 to prevent autoimmune diabetes in Mice. *Pharm Res-Dord* 26(1):72-81.
45. Getts D R, et al. (2012) Microparticles bearing encephalitogenic peptides induce T-cell tolerance and ameliorate experimental autoimmune encephalomyelitis. *Nat biotechnol* 30(12):1217-1224.
46. Kim W U, et al. (2002) Suppression of collagen-induced arthritis by single administration of poly(lactic-co-glycolic acid) nanoparticles entrapping type II collagen—A novel treatment strategy for induction of oral tolerance. *Arthritis Rheum-Us* 46(4):1109-1120.
47. Fang R H, et al. (2013) Lipid-insertion enables targeting functionalization of erythrocyte membrane-cloaked nanoparticles. *Nanoscale* 5(19):8884-8888.membrane-cloaked nanoparticles. *Nanoscale* 5:8884-8888.
48. Hu C M J, Fang R H, Luk B T, & Zhang L (2014) Polymeric nanotherapeutics: clinical development and advances in stealth functionalization strategies. *Nanoscale* 6(1):65-75.

What is claimed is:

1. A method for reducing anemia symptoms in a subject, which method comprises:
    administering, to a subject in need, an effective amount of a nanoparticle comprising a) an inner core comprising a non-cellular material, and b) an outer surface comprising a plasma membrane isolated from a red blood cell (RBC) comprising a self-antigen that comprises glycophorin A and targets an anti-RBC autoantibody that causes anemia,
    wherein said subject suffers from hemolytic anemia caused by opsonization of RBC with said anti-RBC auto-antibody, and said nanoparticle sequesters or neutralizes said anti-RBC autoantibody in said subject and reduces anemia symptoms in said subject.

2. The method of claim 1, wherein the subject is a human.

3. The method of claim 1, wherein the inner core comprises a biocompatible or a synthetic material selected from the group consisting of poly(lactic-co-glycolic acid (PLGA), polylactic acid (PLA), polyglycolic acid (PGA), polycaprolactone (PCL), polylysine, and polyglutamic acid.

4. The method of claim 1, wherein the inner core supports the outer surface.

5. The method of claim 1, wherein the nanoparticle further comprises a releasable cargo.

6. The method of claim 1, wherein the nanoparticle has a diameter from about 10 nm to about 10 µm.

7. The method of claim 1, wherein the nanoparticle substantially lacks constituents of the cell from which the plasma membrane is derived.

8. The method of claim 1, wherein the nanoparticle substantially maintains natural structural integrity or activity of the plasma membrane or the constituents of the plasma membrane.

9. The method of claim 1, wherein the nanoparticle is biocompatible or biodegradable.

10. The method of claim 1, wherein the nanoparticle substantially lacks immunogenicity to the subject.

11. The method of claim 10, wherein the plasma membrane is isolated from a cell from the same species of the subject.

12. The method of claim 1, further comprising administering another active ingredient to the subject.

13. The method of claim 1, wherein the nanoparticle does not comprise a drug payload to suppress normal lymphocytes or immune effector cells in a subject.

\* \* \* \* \*